United States Patent
Ohi et al.

(10) Patent No.: US 7,390,797 B2
(45) Date of Patent: Jun. 24, 2008

(54) FUSED INDAZOLE COMPOUNDS

(75) Inventors: Norihito Ohi, Ibaraki (JP); Nobuaki Sato, Ibaraki (JP); Naohiro Kohmura, Ibaraki (JP)

(73) Assignee: Eisai Co., Ltd., Bunkyo-ku, Tokyo (JP)

( * ) Notice: Subject to any disclaimer, the term of this patent is extended or adjusted under 35 U.S.C. 154(b) by 367 days.

(21) Appl. No.: 10/503,216

(22) PCT Filed: Feb. 21, 2003

(86) PCT No.: PCT/JP03/01941

§ 371 (c)(1), (2), (4) Date: Sep. 6, 2005

(87) PCT Pub. No.: WO03/072550

PCT Pub. Date: Sep. 4, 2003

(65) Prior Publication Data

US 2006/0111419 A1    May 25, 2006

(30) Foreign Application Priority Data

Feb. 28, 2002  (JP) .............................. 2002-052890

(51) Int. Cl.
| A61K 31/416 | (2006.01) |
| A61K 31/4162 | (2006.01) |
| A61K 31/55 | (2006.01) |
| A61K 31/551 | (2006.01) |
| A61K 31/553 | (2006.01) |
| A61K 31/554 | (2006.01) |
| C07D 231/54 | (2006.01) |
| C07D 245/04 | (2006.01) |
| C07D 243/10 | (2006.01) |
| C07D 225/04 | (2006.01) |
| C07D 223/14 | (2006.01) |
| C07D 267/04 | (2006.01) |

(52) U.S. Cl. .............................. 514/211.04; 514/212.05; 514/215; 514/405; 548/358.1; 548/358.5; 540/555; 540/546; 540/578

(58) Field of Classification Search .................. None
See application file for complete search history.

(56) References Cited

U.S. PATENT DOCUMENTS 4,013,672 A    3/1977  Hoehn

FOREIGN PATENT DOCUMENTS

| WO | WO-00/08139 A1 | 4/2000 |
| WO | WO-00/18407 A1 | 4/2000 |
| WO | WO-00/35906 A2 | 6/2000 |
| WO | WO-00/35921 A1 | 6/2000 |
| WO | WO-01/12609 A1 | 2/2001 |
| WO | WO-02/10137 A2 | 2/2002 |
| WO | WO-02/066450 A2 | 8/2002 |
| WO | WO-02/083648 A1 | 10/2002 |

OTHER PUBLICATIONS

O'Neill, Luk A. J. Targeting signal transduction as a strategy to treat inflammatory diseases, Nature Reviews. Drug Discovery. London: Jul. 2006. vol. 5, Iss. 7; p. 549.*
Kyriakis et al., Nature, vol. 369, pp. 156-160, (1994).
Xia et al., Science, vol. 270, pp. 1326-1331, (1995).
Pulverer et al., Nature, vol. 353, pp. 674, (1995).
Mohit et al., Neuron, vol. 14, pp. 67-78, (1995).
Kuan et al., Neuron, vol. 22, pp. 667-676, (1999).
Sabapathy et al., J. Exp. Med., vol. 193, pp. 317-328, (2001).
Yang et al., Nature, vol. 389, pp. 865-870, (1997).
Smale et al, Experimental Neurology, vol. 133, pp. 225-230, (1995).
Mochizuki et al., Journal of Neurological Sciences, vol. 137, pp. 120-123, (1996).
Zhu et al., J. Neurochem., vol. 76, pp. 435-441, (2001).
Hollins et al., Journal of Heterocyclic Chemistry, vol. 16, No. 4, pp. 681-683, (1979).

\* cited by examiner

*Primary Examiner*—Rebecca L Anderson
*Assistant Examiner*—Michael P Barker
(74) *Attorney, Agent, or Firm*—Birch, Stewart, Kolasch & Birch, LLP

(57) ABSTRACT

The present invention provides a novel fused indazole compound having an excellent JNK inhibitory action. More specifically, it provides a compound represented by the following formula, a salt thereof or a hydrate of them.

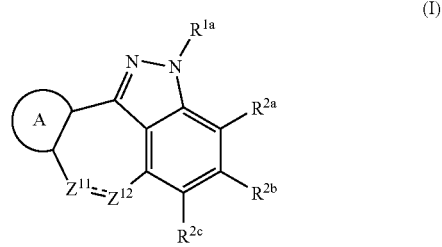

(I)

Wherein $Z^{11}$ and $Z^{12}$ each independently represent a carbonyl group, a methylene group, etc.; ----- represents a double bond or a single bond; $R^{1a}$ represents a hydrogen atom, etc.; the ring A represents a benzene ring, a naphthalene ring or a 5- to 10-membered aromatic heterocyclic ring, etc.; and $R^{2a}$, $R^{2b}$ and $R^{2c}$ each independently represent (1) a hydrogen atom, (2) a halogen atom, (3) a nitro group, etc.

14 Claims, No Drawings

FUSED INDAZOLE COMPOUNDS

TECHNICAL FIELD

The present invention relates to a novel fused indazole compound having an excellent inhibitory action on protein phosphatase (protein kinase), especially on JNK protein kinase.

PRIOR ART

A cascade by action of mitogen-activated protein kinase (hereinafter referred to as "MAPK") is universally presents from yeasts to humans and plays a very important role as one of intracellular signaling pathways. Among such MAPK-related kinases in mammalian cells, three types of kinases, namely, extracellular signal-regulation kinase (ERK), p38, and c-Jun amino-terminal kinase (JNK; or also referred to as stress-activated protein kinases (SAPK)) are particularly well known. SAPKs have been found in rats and are JNK homologues, and it is known that isoform groups thereof each have an amino acid sequence 90% or more equivalent to that of a corresponding isoform group of JNKs (Nature, 369, 156, 1994). A multitude of activators relating to MAPK have been identified recently, and it has been clarified that pathways for activating ERK, p38, and JNKs play functionally different roles, respectively. Especially, the JNK system is considered to play a role as one of medically and pharmaceutically worthy intracellular signaling pathways for the following reasons. The JNK system is possibly an important signaling pathway that is activated by, for example, stress factors to cells, such as tumor necrosis factor α (TNF-α), interleukin-1 (IL-1), and other cytokines, as well as heat shock, ultraviolet rays (UV), and X-rays, and induces not only cell proliferation and/or differentiation but also apoptosis (cell death) (Science, 270, 1326, 1995). JNKs were first found as a kinase for phosphatasing orylating Ser 63 and Ser 73 at the N-terminus of c-Jun (Nature, 353, 670, 1991), but in recent, it has been clarified that JNKs phosphorylate many transcription factors such as ATF-2 and Elk-1 and regulate their activities (EM-BOJ., 15, 2760, 1996). JNKs include three types, JNK 1, JNK 2 and JNK 3. JNK 1 and JNK 2 are expressed in most of tissues, but JNK 3 is particularly highly expressed in the brain (Neuron, 14, 67, 1995; Neuron, 22, 667, 1999). Analyses of knocked out mice lacking JNK 1 or JNK 2 have revealed that these JNKs play important roles in differentiation and/or activation of T cells (J. Exp. Med., 193, 317, 2001). In contrast, it has been reported that JNK 3-deficient mice are resistant to seizure induced by kainic acid, an excitable amino acid receptor agonist. Further, it has been also reported that JNK 3-deficient mice do not show apoptosis, which apoptosis is found in hippocampus neuron of wild-type mice after such seizure (nature 389, 865, 1997). Neuronal cell death due to apoptosis is speculated to play an important role in neuronal degeneration processes in neurodegenerative diseases such as Alzheimer's disease and Parkinson's disease (Experimental Neurology 133, 225, 1995; J. Neurol. Sci. 137, 120, 1996), and results suggesting the possibility that JNKs are involved in the neuronal cell death have been accumulated (Neuron, 14, 67, 1995; J. Neurochem., 76, 435, 2001).

For example, the following reports have been made on low-molecular substances having JNK inhibitory action.

(1) Compounds represented by the formula ($I^1$) having JNK inhibitory action (WO 02/10137);

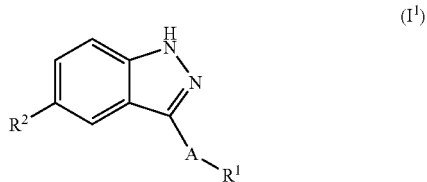

(2) compounds represented by the formula ($I^2$) having JNK inhibitory action (WO 02/083648);

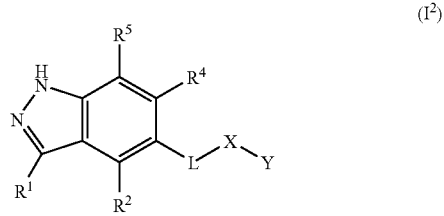

(3) compounds represented by the formula ($I^3$) having JNK inhibitory action, and compounds represented by the formula ($I^{3a}$) as specific embodiments thereof (WO 01/12609);

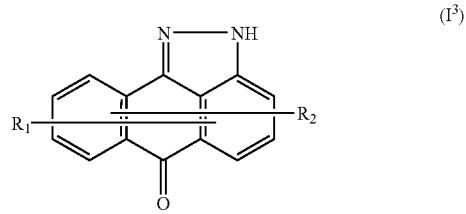

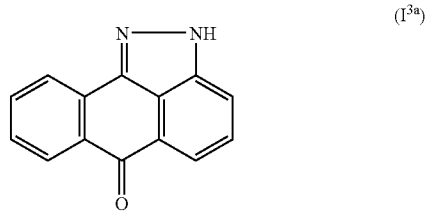

(4) compounds represented by the formula (I⁴) having JNK inhibitory action, and compounds represented by the formula (I⁴ᵃ) as specific embodiments thereof (WO 02/66450).

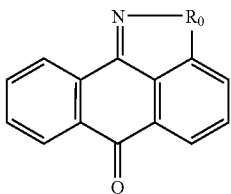

(I⁴)

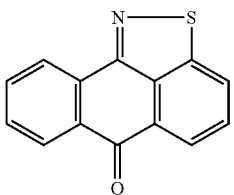

(I⁴ᵃ)

In contrast, compound represented by the following formula:

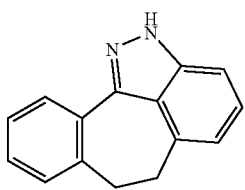

(6,7-dihydrobenzo[1,2]cyclohepta[3,4,5-cd]indazole) has been reported in J. Heterocyclic Chem., 16, 681 (1979), but the relation with pharmaceuticals or pharmacological actions such as JNK protein kinase inhibitory action has not yet been reported at all.

As is described above, the JNK system receives attention as one of important mechanisms relating to activation of various cells, regulation of immunocytes, or apoptosis of neurons induced by various stress signals. Accordingly, compounds exhibiting inhibitory action on the JNK pathway, particularly on JNK protein kinases are expected to be useful as therapeutic agents for various immunologic diseases, inflammatory diseases, and/or neurodegenerative diseases. However, compounds having excellent JNK protein kinase inhibitory action and satisfying requirements in, for example, pharmacological activities, dosage, and safety as pharmaceutical drugs have not yet been found.

DISCLOUSRE OF THE INVENTION

After intensive investigations under these circumstances, the present inventors have found novel fused indazole compounds having JNK inhibitory action. That is, the present invention relates to:

<1> a compound represented by the formula:

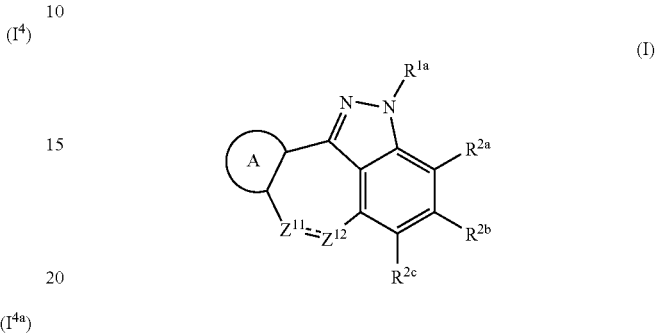

(I)

(wherein $Z^{11}$ and $Z^{12}$ each independently represent a carbonyl group, an oxygen atom, a sulfur atom, a methine group which may be substituted, a methylene group which may be substituted or a nitrogen atom which may be substituted;- - - - - represents a double bond or a single bond; $R^{1a}$ represents a hydrogen atom, a $C_1$-$C_6$ alkyl group, a phenyl group or a benzyl group; $R^{2a}$, $R^{2b}$ and $R^{2c}$ each independently represent a group selected from the following Substituent Group (a); the ring A represents a benzene ring which may have one to three groups selected from the following Substituent Group (a), a naphthalene ring which may have one to three groups selected from the following Substituent Group (a) or a 5- to 10-membered aromatic heterocyclic ring which may have one to three groups selected from the following Substituent Group (a);

Substituent Group (a)

(1) a hydrogen atom, (2) halogen atoms, (3) a nitro group, (4) a hydroxyl group, (5) a cyano group, (6) a carboxyl group, (7) an amino group, (8) a formyl group or (9) a group represented by the formula:

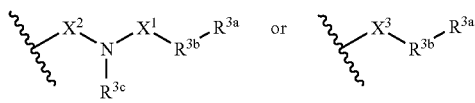

(wherein $X^1$ and $X^2$ each independently represent a single bognd, —CO—, —SO₂— or $C_1$-$C_6$-methylene group; $X^3$ represents a single bond, —CO—, —SO₂, —O—, —CO—O— or —O—CO—; $R^{3b}$ represents a $C_1$-$C_6$ alkylene group or a single bond; $R^{3a}$ and $R^{3c}$ represent a hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_8$ cycloalkyl group which may be substituted, a $C_6$-$C_{14}$ aromatic cyclic hydrocarbon group which may be substituted, a 5- to 14-membered aromatic heterocyclic group which may be substituted or a hydrogen atom), provided that 6,7-dihydrobenzo[1,2]cyclohepta[3,4,5-cd]indazole is excluded), a salt thereof or a hydrate of them;

<2> a compound represented by the formula:

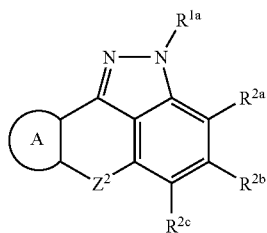

(II)

(wherein $Z^2$ represents a 1,2-ethylene group which may be substituted, a 1,2-vinylene group which may be substituted, an oxymethylene group which may be substituted, an aminomethylene group which may be substituted, an amide group which may be substituted or an ester group; and the ring A, $R^{1a}$, $R^{2a}$, $R^{2b}$ and $R^{2c}$ have the same meanings as the ring A, $R^{1a}$, $R^{2a}$, $R^{2b}$ and $R^{2c}$ described in the above-mentioned <1>, provided that 6,7-dihydrobenzo[1,2]cyclohepta[3,4,5-cd]indazole is excluded), a salt thereof or a hydrate of them;

<3> a compound represented by the formula:

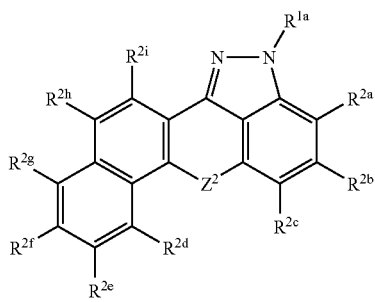

(III)

(wherein $R^{1a}$, $R^{2a}$, $R^{2b}$ and $R^{2c}$ have the same meanings as $R^{1a}$, $R^{2a}$, $R^{2b}$ and $R^{2c}$ described in the above-mentioned <1>, respectively; $Z^2$ has the same meaning as $Z^2$ described in the above-mentioned <2>; and $R^{2d}$, $R^{2e}$, $R^{2f}$, $R^{2g}$, $R^{2h}$ and $R^{2i}$ each independently represent a substituent selected from the Substituent Group (a) described in the above-mentioned <1>), a salt thereof or a hydrate of them;

<4> a compound represented by the formula:

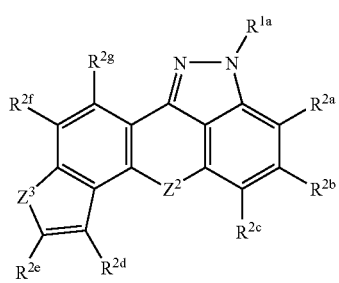

(IV)

(wherein $R^{1a}$, $R^{2a}$, $R^{2b}$ and $R^{2c}$ have the same meanings as $R^{1a}$, $R^{2a}$, $R^{2b}$ and $R^{2c}$ described in the above-mentioned <1>, respectively; $Z^2$ has the same meaning as $Z^2$ described in the above-mentioned <2>; $R^{2d}$, $R^{2e}$, $R^{2f}$ and $R^{2g}$ each independently represent a substituent selected from the Substituent Group (a) described in the above-mentioned <1>; and $Z^3$ represents a nitrogen atom, an oxygen atom, a sulfur atom or a group represented by the formula —$NR^{4b}$— (wherein $R^{4b}$ represents a hydrogen atom or a $C_1$-$C_6$ alkyl group)), a salt thereof or a hydrate of them;

<5> a compound represented by the formula:

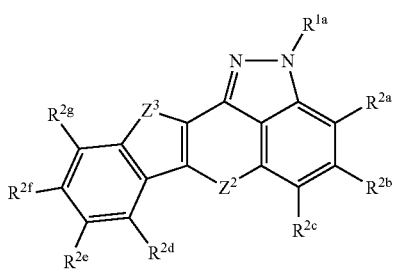

(V)

(wherein $R^{1a}$, $R^{2a}$, $R^{2b}$ and $R^{2c}$ have the same meanings as $R^{1a}$, $R^{2a}$, $R^{2b}$ and $R^{2c}$ described in the above-mentioned <1>, respectively; $Z^2$ has the same meaning as $Z^2$ described in the above-mentioned <2>; $R^{2d}$, $R^{2e}$, $R^{2f}$ and $R^{2g}$ each independently represent a substituent selected from the Substituent Group (a) described in the above-mentioned <1>; and $Z^3$ has the same meaning as $Z^3$ described in the above-mentioned <4>), a salt thereof or a hydrate of them;

<6> a compound represented by the formula:

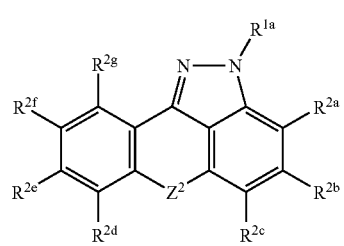

(VI)

(wherein $R^{1a}$, $R^{2a}$, $R^{2b}$ and $R^{2c}$ have the same meanings as $R^{1a}$, $R^{2a}$, $R^{2b}$ and $R^{2c}$ described in the above-mentioned <1>, respectively; $Z^2$ has the same meaning as $Z^2$ described in the above-mentioned <2>; and $R^{2d}$, $R^{2e}$, $R^{2f}$ and $R^{2g}$ each independently represent a substituent selected from the Substituent Group (a) described in the above-mentioned <1>, provided that 6,7-dihydrobenzo[1,2]cyclohepta[3,4,5-cd]indazole is excluded), a salt thereof or a hydrate of them;

<7> the compound according to any one of the above-mentioned <3> to <6>, a salt thereof or a hydrate of them, wherein at least five of $R^{2a}$, $R^{2b}$, $R^{2c}$, $R^{2d}$, $R^{2e}$, $R^{2f}$ and $R^{2g}$ are hydrogen atoms;

<8> the compound according to any one of the above-mentioned <2> to <7>, a salt thereof or a hydrate of them, wherein $Z^2$ is a 1,2-ethylene group, a 1,2-vinylene group, a group represented by the formula —CO—$NR^{4a}$— (wherein $R^{4a}$ represents a hydrogen atom or a $C_1$-$C_6$ alkyl group) or a group represented by the formula —$NR^{4a}$—CO— (wherein $R^{4a}$ represents a hydrogen atom or a $C_1$-$C_6$ alkyl group);

<9> the compound according to the above-mentioned <1> or <2>, a salt thereof or a hydrate of them, wherein the ring A is a benzene ring which may have one to three groups selected from the Substituent Group (a) described in the above-mentioned <1>, a naphthalene ring which may have one to three groups selected from the Substituent Group (a) described in the above-mentioned <1>, an indole ring which may have one to three groups selected from the Substituent Group (a) described in the above-mentioned <1>, a benzofuran ring which may have one to three groups selected from the Substituent Group (a) described in the above-mentioned <1>, a benzothiophene ring which may have one to three groups selected from the Substituent Group (a) described in the above-mentioned <1>, a pyridine ring which may have one to three groups selected from the Substituent Group (a) described in the above-mentioned <1>, a furan ring which may have one to three groups selected from the Substituent Group (a) described in the above-mentioned <1>, or a thiophene ring which may have one to three groups selected from the Substituent Group (a) described in the above-mentioned <1>;

<10> the compound according to any one of the above-mentioned <1>, <2> and <9>, a salt thereof or a hydrate of them, wherein the ring A is a ring having one group selected from the Substituent Group (a) described in the above-mentioned <1>;

<11> the compound according to any one of the above-mentioned <1> to <10>, a salt thereof or a hydrate of them, wherein $R^{1a}$ is a hydrogen atom;

<12> the compound according to any one of the above-mentioned <1> to <11>, a salt thereof or a hydrate of them, wherein $R^{2a}$ and $R^{2b}$ are hydrogen atoms;

<13> a c-Jun amino-terminal kinase (JNK) inhibitor, comprising the compound according to any one of the above-mentioned <1> to <12>, a salt thereof or a hydrate of them;

<14> a c-Jun amino-terminal kinase 1 (JNK 1), c-Jun amino-terminal kinase 2 (JNK 2) and/or c-Jun amino-terminal kinase 3 (JNK 3) inhibitor, comprising the compound according to any one of the above-mentioned <1> to <12>, a salt thereof or a hydrate of them;

<15> an agent for treating or preventing an immunologic disease, inflammatory disease and/or neurodegenerative disease, comprising the compound according to any one of the above-mentioned <1> to <12>, a salt thereof or a hydrate of them;

<16> an agent for treating or preventing Alzheimer's disease, Parkinson's disease, L-DOPA-induced dyskinesia in treatment of Parkinson's disease, Huntington's chorea, neurodegenerative diseases such as multiple sclerosis, amyotrophic lateral sclerosis, ischemic disease, brain disorder in cerebral stroke, schizophrenia, depression, epilepsy, an immunologic disease or inflammatory disease, comprising the compound according to any one of the above-mentioned <1> to <12>, a salt thereof or a hydrate of them; <17> use of the compound according to any one of the above-mentioned <1> to <12> or a salt thereof, for therapy or prophylaxis of an immunologic disease, inflammatory disease and/or neurodegenerative disease;

<18> the agent for treating or preventing according to the above-mentioned <15>, wherein the immunologic disease or inflammatory disease is septicemia, chronic rheumatoid arthritis, osteoarthritis, gout, psoriasis, psoriatic arthropathy, bronchitis, chronic obstructive pulmonary diseases, cystic pulmonary fibrosis, insulin-dependent type I diabetes, autoimmune thyroiditis, Crohn disease, ulcerative colitis, atopic dermatitis, asthma, allergic rhinitis, hepatitis, systemic erythematosus, acute and chronic graft rejection after organ transplantation, graft versus host diseases, eczema, urticaria, myasthenia gravis, acquired immunologic deficiency syndrome, idiopathic thrombocytopenic purpura or glomerulonephritis;

<19> an agent for treating or preventing a neurodegenerative disease, comprising the compound according to any one of the above-mentioned <1> to <12>, a salt thereof or a hydrate of them;

<20> the agent for treating or preventing according to the above-mentioned <19>, wherein the neurodegenerative disease is acute neurodegenerative disease;

<21> the agent for treating or preventing according to the above-mentioned <20>, wherein the acute neurodegenerative disease is an acute stage of cerebrovascular disorder, head injury, spinal code injury, neuropathy due to hypoxia or hypoglycemia;

<22> the agent for treating or preventing according to the above-mentioned <19>, wherein the neurodegenerative disease is chronic neurodegenerative disease;

<23> the agent for treating or preventing according to the above-mentioned <19>, wherein the neurodegenerative disease is epilepsy, hepatic encephalopathy, peripheral neuropathy, Parkinsonian syndrome, spastic paralysis, pain or neuralgia;

<24> the agent for treating or preventing according to the above-mentioned <19>, wherein the neurodegenerative disease is infectious encephalomyelitis, cerebrovascular dementia, dementia or neurosis due to meningitis;

<25> the agent for treating or preventing according to the above-mentioned <24>, wherein the infectious encephalomyelitis is HIV encephalomyelitis;

<26> use of the compound according to any one of the above-mentioned <1> to <12>, a salt thereof or a hydrate of them, for treating or preventing an immunologic disease, inflammatory disease and/or neurodegenerative disease;

<27> use of the compound according to any one of the above-mentioned <1> to <12>, a salt thereof or a hydrate of them, for producing an agent for treating an immunologic disease, inflammatory disease and/or neurodegenerative disease;

<28> use of the compound according to any one of the above-mentioned <1> to <12>, a salt thereof or a hydrate of them, for producing a c-Jun amino-terminal kinase 3 (JNK 3) inhibitor, etc.

The present invention provides a method for treating or preventing a disease against which inhibition of a c-Jun amino-terminal kinase (JNK) is effective, which comprises administering a pharmacologically effective amount of the compound according to any one of the above <1> to <12>, a salt thereof or a hydrate of them to a patient.

The present invention further provides use of the compound according any one of the above <1> to <12>, a salt thereof or a hydrate of them, for producing an agent for treating or preventing a disease against which inhibition of a c-Jun amino-terminal kinase (JNK) is effective.

The meanings of symbols, terms etc. as used in the present description will be described, and the present invention will be illustrated in detail below.

The term "and/or" as used in the present description means and includes both the cases of "and" and "or".

The term "JNK" as used in the present description means an enzyme that phosphorylates the N-terminus region of a c-Jun protein and includes, for example, JNK 1, JNK 2, and JNK 3. Such JNKs include three types, JNK 1, JNK 2 and JNK 3. JNK 1 and JNK 2 are expressed in most of tissues, but JNK 3 is particularly highly expressed in the brain (Neuron, 14, 67, 1995; Neuron, 22, 667, 1999).

The term "neurodegenerative disease(s)" as used in the present description means all of diseases generally classified as neurodegenerative diseases in the field of medicine and includes, but is not specifically limited to, chronic or acute neurodegenerative diseases such as subarachnoid hemorrhage, acute stage of cerebrovascular disorder, head injury, spinal code injury, neuropathy due to hypoxia or hypoglycemia, Alzheimer's disease, Parkinson's disease, Huntington's chorea, amyotrophic diseases (e.g., amyotrophic lateral sclerosis), spinocerebellar degeneration, epilepsy, hepatic encephalopathy, peripheral neuropathy, Parkinsonian syndrome, spastic paralysis, pain, neuralgia, schizophrenia, depression, anxiety, drug dependence, nausea, vomiting, urination disorder, visual disorder due to glaucoma, hearing disorder due to antibiotics, food posisoning or multiple sclerosis.

The term "immunologic disease(s)" as used in the present description means all of diseases classified as immunologic diseases in the field of medicine and are not specifically limited. The term "inflammatory disease(s)" as used in the present description means and includes all of diseases classified as inflammatory diseases in the field of medicine and are not specifically limited.

In the specification of the present invention, there is the case where the structural formula of a compound represents a definite isomer. However, the present invention includes isomers such as geometrical isomers, optical isomers based on asymmetric carbon, stereoisomers and tautomers and is not limited by the description of the formula illustrated for the sake of convenience. Accordingly, although it is possible that an asymmetric carbon atom is present in a molecule and accordingly that optically active substance and racemic substance may be present, the present invention is not limited thereto but covers any of them. Further, crystal polymorphism may be present but, again, there is no limitation but any of single crystal form or a mixture will do. The compound (I) or its salt related to the present invention may be an anhydride or a hydrate, and either of them are included in the scope of claim for patent in the present invention. The metabolite which is generated by decomposing the compound (I) related to the present invention in vivo, and the prodrug of the compound (I) or its salt related to the present invention produce are also included in the scope of claim for patent in the present invention.

The term "halogen atom(s)" as used in the present description includes, for example, a fluorine atom, chlorine atom, bromine atom, and iodine atom, preferably a fluorine atom, chlorine atom and bromine atom.

The term "$C_1$-$C_6$ alkyl group(s)" as used in the present description means an alkyl group containing 1 to 6 carbon atoms, and preferred examples include linear or branched alkyl groups such as methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, 2-ethylpropyl group, n-hexyl group, 1-methyl-2-ethylpropyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group or 3-methylpentyl group. More preferred examples are methyl group, ethyl group, n-propyl group, iso-propyl group, n-butyl group, iso-butyl group, sec-butyl group, tert-butyl group and n-pentyl group.

The term "$C_1$-$C_6$ alkylene group(s)" as used in the present description means a divalent group derived from the above-defined "$C_1$-$C_6$ alkyl group" by removal of one hydrogen atom at an arbitrary position and includes, for example, methylene group, ethylene group, methylethylene group, propylene group, ethylethylene group, 1,1-dimethylethylene group, 1,2-dimethylethylene group, trimethylene group, 1-methyltrimethylene group, 1-ethyltrimethylene group, 2-methyltrimethylene group, 1,1-dimethyltrimethylene group, tetramethylene group, pentamethylene group and hexamethylene group.

The term "$C_2$-$C_6$ alkenyl group(s)" as used in the present description means an alkenyl group containing 2 to 6 carbon atoms and preferred examples are vinyl group, allyl group, 1-propenyl group, 2-propenyl group, isopropenyl group, 2-methyl-1-propenyl group, 3-methyl-1-propenyl group, 2-methyl-2-propenyl group, 3-methyl-2-propenyl group, 1-butenyl group, 2-butenyl group, 3-butenyl group, 1-pentenyl group, 1-hexenyl group, 1,3-hexadienyl group and 1,6-hexadienyl group.

The term "$C_2$-$C_6$ alkynyl group(s)" as used in the present description means an alkynyl group containing 2 to 6 carbon atoms, and preferred examples are ethynyl group, 1-propynyl group, 2-propynyl group, 1-butynyl group, 2-butynyl group, 3-butynyl group, 3-methyl-1-propynyl group, 1-ethynyl-2-propynyl group, 2-methyl-3-propynyl group, 1-pentynyl group, 1-hexynyl group, 1,3-hexadiynyl group and 1,6-hexadiynyl group.

The term "$C_3$-$C_8$ cycloalkyl group(s)" as used in the present description means a cycloalkyl group containing 3 to 8 carbon atoms and includes, for example, cyclopropyl group, cyclobutyl group, cyclopentyl group, cyclohexyl group, cycloheptyl group and cyclooctyl group.

The term "$C_1$-$C_6$ alkoxy group(s)" as used in the present description means an alkoxy group containing 1 to 6 carbon atoms, and preferred examples thereof are methoxy group, ethoxy group, n-propoxy group, iso-propoxy group, sec-propoxy group, n-butoxy group, iso-butoxy group, sec-butoxy group, tert-butoxy group, n-pentyloxy group, iso-pentyloxy group, sec-pentyloxy group, n-hexoxy group, iso-hexoxy group, 1,1-dimethylpropyloxy group, 1,2-dimethylpropoxy group, 2,2-dimethylpropyloxy group, 2-ethylpropoxy group, 1-methyl-2-ethylpropoxy group, 1-ethyl-2-methylpropoxy group, 1,1,2-trimethylpropoxy group, 1,1,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutyloxy group, 2-ethylbutoxy group, 1,3-dimethylbutoxy group, 2-methylpentoxy group, 3-methylpentoxy group and hexyloxy group.

Preferred examples of the "$C_1$-$C_6$ alkylcarbamoyl group(s)" as used in the present description are methylcarbamoyl group, ethylcarbamoyl group, n-propylcarbamoyl group, iso-propylcarbamoyl group, n-butylcarbamoyl group, iso-butylcarbamoyl group, sec-butylcarbamoyl group, tert-butylcarbamoyl group, n-pentylcarbamoyl group, 1,1-dimethylpropylcarbamoyl group, 1,2-dimethylpropylcarbamoyl group, 2,2-dimethylpropylcarbamoyl group, 1-ethylpropylcarbamoyl group, 2-ethylpropylcarbamoyl group, n-hexylcarbamoyl group, 1-methyl-2-ethylpropylcarbamoyl group, 1-ethyl-2-methylpropylcarbamoyl group, 1,1,2-trimethylpropylcarbamoyl group, 1-propylpropylcarbamoyl group, 1-methylbutylcarbamoyl group, 2-methylbutylcarbamoyl group, 1,1-dimethylbutylcarbamoyl group, 1,2-dimethylbutylcarbamoyl group, 2,2-dimethylbutylcarbamoyl group, 1,3-dimethylbutylcarbamoyl group, 2,3-dimethylbutylcarbamoyl group, 2-ethylbutylcarbamoyl group, 2-methylpentylcarbamoyl group and 3-metylpentylcarbamoyl group.

The term "$C_1$-$C_6$ alkoxycarbonyl group(s)" as used in the present description means a carbonyl group combined with the above-defined "$C_1$-$C_6$ alkoxy group" and includes, for example, methoxycarbonyl group, ethoxycarbonyl group, n-propoxycarbonyl group, i-propoxycarbonyl group, n-butoxycarbonyl group, i-butoxycarbonyl group, sec-butoxycarbonyl group and t-butoxycarbonyl group.

The term "$C_2$-$C_7$ acyl group(s)" as used in the present description means an atomic group derived from a fatty acid containing 2 to 7 carbon atoms by removal of OH group, and preferred examples are acetyl group, propionyl group and butyroyl group.

Preferred examples of the "$C_1$-$C_6$ alkylcarbonyloxy group(s)" as used in the present description are methylcarbonyloxy group, ethylcarbonyloxy group, n-propylcarbonyloxy group, iso-propylcarbonyloxy group, n-butylcarbonyloxy group, iso-butylcarbonyloxy group, sec-butylcarbonyloxy group, tert-butylcarbonyloxy group, n-pentylcarbonyloxy group, 1,1-dimethylpropylcarbonyloxy group, 1,2-dimethylpropylcarbonyloxy group, 2,2-dimethylpropylcarbonyloxy group, 1-ethylpropylcarbonyloxy group, 2-ethylpropylcarbonyloxy group, n-hexylcarbonyloxy group, 1-methyl-2-ethylpropylcarbonyloxy group, 1-ethyl-2-methylpropylcarbonyloxy group, 1,1,2-trimethylpropylcarbonyloxy group, 1-propylpropylcarbonyloxy group, 1-methylbutylcarbonyloxy group, 2-methylbutylcarbonyloxy group, 1,1-dimethylbutylcarbonyloxy group, 1,2-dimethylbutylcarbonyloxy group, 2,2-dimethylbutylcarbonyloxy group, 1,3-dimethylbutylcarbonyloxy group, 2,3-dimethylbutylcarbonyloxy group, 2-ethylbutylcarbonyloxy group, 2-methylpentylcarbonyloxy group and 3-metylpentylcarbonyloxy group.

Preferred examples in the "$C_1$-$C_6$ alkylsulfonyl group(s)" as used in the present description are methylsulfonyl group, ethylsulfonyl group, n-propylsulfonyl group, iso-propylsulfonyl group, n-butylsulfonyl group, iso-butylsulfonyl group, sec-butylsulfonyl group, tert-butylsulfonyl group, n-pentylsulfonyl group, 1,1-dimethylpropylsulfonyl group, 1,2-dimethylpropylsulfonyl group, 2,2-dimethylpropylsulfonyl group, 1-ethylpropylsulfonyl group, 2-ethylpropylsulfonyl group, n-hexylsulfonyl group, 1-methyl-2-ethylpropylsulfonyl group, 1-ethyl-2-methylpropylsulfonyl group, 1,1,2-trimethylpropylsulfonyl group, 1-propylpropylsulfonyl group, 1-methylbutylsulfonyl group, 2-methylbutylsulfonyl group, 1,1-dimethylbutylsulfonyl group, 1,2-dimethylbutylsulfonyl group, 2,2-dimethylbutylsulfonyl group, 1,3-dimethylbutylsulfonyl group, 2,3-dimethylbutylsulfonyl group, 2-ethylbutylsulfonyl group, 2-methylpentylsulfonyl group and 3-metylpentylsulfonyl group.

Preferred examples in the "$C_1$-$C_6$ alkylsulfenyl group(s)" as used in the present description are methylsulfenyl group, ethylsulfenyl group, n-propylsulfenyl group, iso-propylsulfenyl group, n-butylsulfenyl group, iso-butylsulfenyl group, sec-butylsulfenyl group, tert-butylsulfenyl group, n-pentylsulfenyl group, 1,1-dimethylpropylsulfenyl group, 1,2-dimethylpropylsulfenyl group, 2,2-dimethylpropylsulfenyl group, 1-ethylpropylsulfenyl group, 2-ethylpropylsulfenyl group, n-hexylsulfenyl group, 1-methyl-2-ethylpropylsulfenyl group, 1-ethyl-2-methylpropylsulfenyl group, 1,1,2-trimethylpropylsulfenyl group, 1-propylpropylsulfenyl group, 1-methylbutylsulfenyl group, 2-methylbutylsulfenyl group, 1,1-dimethylbutylsulfenyl group, 1,2-dimethylbutylsulfenyl group, 2,2-dimethylbutylsulfenyl group, 1,3-dimethylbutylsulfenyl group, 2,3-dimethylbutylsulfenyl group, 2-ethylbutylsulfenyl group, 2-methylpentylsulfenyl group and 3-metylpentylsulfenyl group.

Preferred examples in the "$C_1$-$C_6$ alkylthio group(s)" as used in the present description are methylthio group, ethylthio group, n-propylthio group, iso-propylthio group, n-butylthio group, iso-butylthio group, sec-butylthio group, tert-butylthio group, n-pentylthio group, 1,1-dimethylpropylthio group, 1,2-dimethylpropylthio group, 2,2-dimethylpropylthio group, 1-ethylpropylthio group, 2-ethylpropylthio group, n-hexylthio group, 1-methyl-2-ethylpropylthio group, 1-ethyl-2-methylpropylthio group, 1,1,2-trimethylpropylthio group, 1-propylpropylthio group, 1-methylbutylthio group, 2-methylbutylthio group, 1,1-dimethylbutylthio group, 1,2-dimethylbutylthio group, 2,2-dimethylbutylthio group, 1,3-dimethylbutylthio group, 2,3-dimethylbutylthio group, 2-ethylbutylthio group, 2-methylpentylthio group and 3-metylpentylthio group.

The term "$C_6$-$C_{14}$ aromatic cyclic hydrocarbon group(s)" as used in the present description means an aromatic cyclic hydrocarbon group containing 6 to 14 carbon atoms and includes monocyclic groups as well as bicyclic groups, tricyclic groups, and other condensed or fused rings. Examples of these groups include phenyl group, indenyl groups, 1-naphthyl group, 2-naphthyl group, azulenyl groups, heptalenyl groups, biphenyl groups, indacenyl groups, acenaphthyl groups, fluorenyl groups, phenalenyl groups, phenanthrenyl groups, anthracenyl groups, cyclopentacyclooctenyl groups and benzocyclooctenyl groups.

The term "5- to 14-membered aromatic heterocyclic group(s)" as used in the present description means a monocyclic, bicyclic or tricyclic 5- to 14-membered aromatic heterocyclic group containing one or more hetero atoms selected from the group consisting of nitrogen atoms, sulfur atoms and oxygen atoms. Examples of the group include 1) nitrogen-containing aromatic heterocyclic groups such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolidyl group, phthalazyl group, naphthyridinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenazinyl group, imidazopyridinyl group, imidazopyrimidinyl group or pyrazolopyridinyl group; 2) sulfur-containing aromatic heterocyclic groups such as thienyl group or benzothienyl group; 3) oxygen-containing aromatic heterocyclic groups such as furyl group, pyranyl group, cyclopentapyranyl group, benzofuryl group or isobenzofuryl group; and 4) aromatic heterocyclic groups each containing two or more different hetero atoms, such as thiazolyl group, isothiazolyl group, benzothiazolyl group, benzthiadiazolyl group, phenothiazinyl group, isoxazoly group, furazanyl group, phenoxazinyl group, oxazolyl group, isoxazolyl group, benzoxazolyl group, oxadiazolyl group, pyrazoloxazolyl group, imidazothiazolyl group, thienofuranyl group, furopyrrolyl group or pyridoxazinyl group.

The term "5- to 14-membered non-aromatic heterocyclic group(s)" as used in the present description means a monocyclic, bicyclic, or tricyclic 5- to 14-membered non-aromatic heterocyclic group containing one or more heteroatoms selected from the group consisting of nitrogen atoms, sulfur atoms and oxygen atoms. Examples of the group include pyrrolidyl group, pyrrolyl group, piperidyl group, piperazyl group, imidazolyl group, pyrazolidyl group, imidazolidyl group, morpholyl group, tetrahydrofuryl group, tetrahydropyranyl group, aziridinyl group, oxiranyl group and oxathiolanyl group. The non-aromatic heterocyclic group also includes groups derived from a pyridone ring and non-aromatic condensed or fused rings such as groups derived from phthalimide ring, and succinimide ring.

The term "5- to 10-membered aromatic heterocyclic ring(s)" as used in the present description means a monocyclic or bicyclic 5- to 10-membered aromatic heterocyclic ring containing one or more hetero atoms selected from the group consisting of nitrogen atoms, sulfur atoms and oxygen atoms. Examples of the group include pyrrole ring, imidazole ring, pyrazole ring, 1,2,3-triazole ring, pyridine ring, pyridazine ring, pyrimidine ring, pyrazine ring, indole ring, isoindole ring, benzimidazole ring, indazole ring, benzotriazole ring, indolizine ring, quinoline ring, isoqunoline ring, phthalazine ring, quinoxaline ring, quinazoline ring, cinnoline ring, naphthyridine ring, thiophene ring, benzothiophene ring, furan ring, benzofuran ring, thiazole ring, isothiazole ring, benzothiazole ring, oxazole ring, isoxazole ring and benzoxazole ring. Preferred examples of the ring include pyridine ring, indole ring, benzimidazole ring, indazole ring, benzotriazole ring, indolizine ring, quinoline ring, isoquinoline ring, phthalazine ring, quinoxaline ring, quinazoline ring, cinnoline ring, naphthyridine ring, benzothiophene ring, benzofuran ring, benzothiazole ring and benzoxazole ring, and of which pyridine ring benzothiophene ring and benzofuran ring are more preferred.

The term "which may be substituted" as used in the present description has the same meaning as in "may have one or plural substituents in an arbitrary combination at position(s) that can be substituted". Specific examples of the substituent include:

(1) halogen atoms, (2) hydroxyl group, (3) nitrile group, (4) $C_1$-$C_6$ alkyl groups, $C_2$-$C_6$ alkenyl groups, $C_2$-$C_6$ alkynyl groups, $C_3$-$C_8$ cycloalkyl groups and $C_1$-$C_6$ alkoxy groups, each of which may be substituted by one to three halogen atoms or hydroxyl groups, (5) $C_6$-$C_{10}$ aromatic cyclic hydrocarbon groups, (6) 5- to 14-membered aromatic heterocyclic groups, (7) 5- to 14-membered heterocyclic groups, (8) carboxyl group, (9) trifluoromethyl group, (10) $C_1$-$C_6$ alkylcarbamoyl groups, (11) $C_1$-$C_6$ alkoxycarbonyl groups, (12) $C_1$-$C_6$ alkylcarbonyl groups, (13) $C_1$-$C_6$ alkylcarbonyloxy groups, (14) $C_1$-$C_6$ alkylsulfonyl groups, (15) $C_1$-$C_6$ alkylsulfinyl groups, (16) $C_1$-$C_6$ alkylthio groups, (17) nitro group, (18) formyl group, (19) substituents represented by the formula:

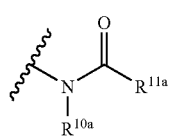

(wherein $R^{10a}$ and $R^{11a}$ each independently represent a hydrogen atom or a $C_1$-$C_6$ alkyl group), (20) substituents represented by the formula:

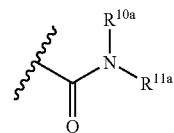

(wherein $R^{10a}$ and $R^{11a}$ each independently represent a hydrogen atom or a $C_1$-$C_6$ alkyl group), and (21) substituents represented by the formula:

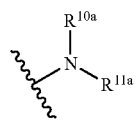

(wherein $R^{10a}$ and $R^{11a}$ each independently represent a hydrogen atom or a $C_1$-$C_6$ alkyl group).

The term "1,2-vinylene group(s)" as used in the present description means a group represented by the formula:

The term "oxymethylene group(s)" as used in the present description means a group represented by the formula:

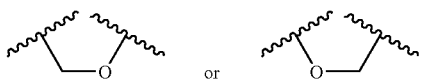

The term "ester group(s)" as used in the present description means a group represented by the formula:

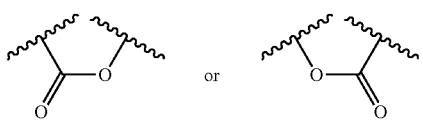

The term "aminomethylene group(s)" as used in the present description means a group represented by the formula:

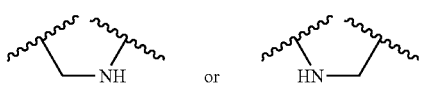

The term "amide group(s)" as used in the present description means a group represented by the formula:

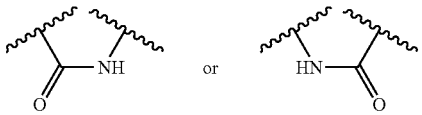

<Meaning of $Z^2$>

In the present description, $Z^2$ represents a 1,2-ethylene group which may be substituted, a 1,2-vinylene group which may be substituted, an oxymethylene group which may be substituted, a thiomethylene group which may be substituted, an aminomethylene group which may be substituted, an amide group which may be substituted or an ester group. Specifically, the compound of the above-mentioned formula (II) is a compound represented by the formula:

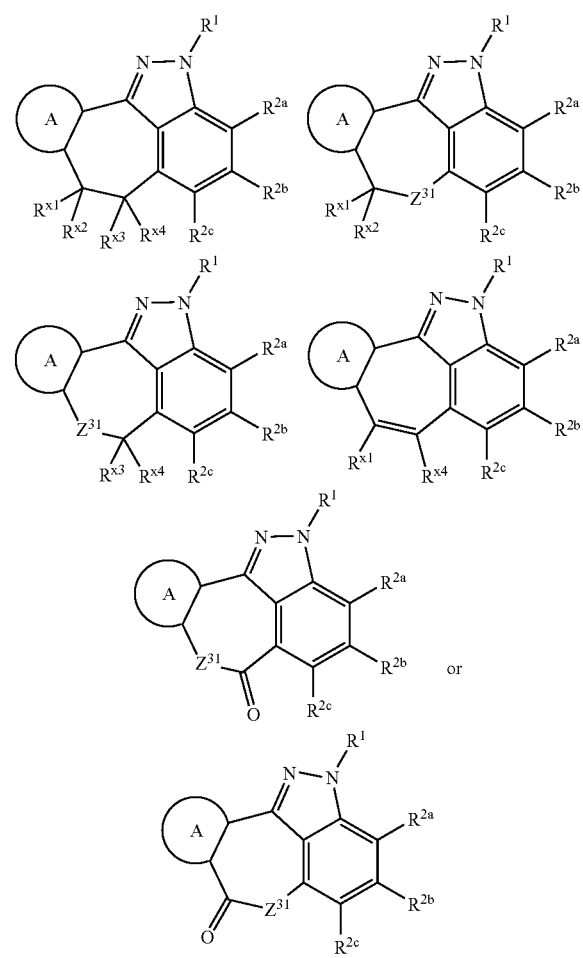

wherein $Z^{31}$ represents an oxygen atom or the formula —$NR^{x5}$—; $R^{x1}$, $R^{x2}$, $R^{x3}$, $R^{x4}$ and $R^{x5}$ each represent a substituent selected from the <Substituent Group (a)>; and the ring A, $R^{1a}$, $R^{2a}$, $R^{2b}$ and $R^{2c}$ have the same meanings as defined above.

They are preferably compounds represented by the formula:

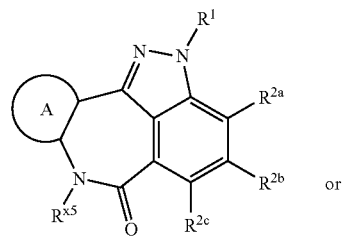

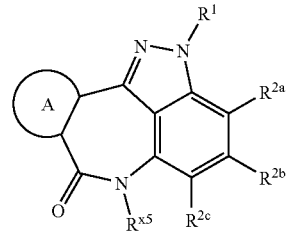

wherein each symbol has the same meaning as defined above.

General Synthesis Method

Typical production processes of the fused indazole compounds represented by the formula (I) according to the present invention will be illustrated below. In the reaction schemes of the following production processes, $R^1$, $R^2$, $R^3$, $R^4$, $R^5$, $R^6$, $R^7$ and $R^9$ each independently represent, for example, a substituent selected from the <Substituent Group (a)>; $R^8$ represents, for example, a $C_1$-$C_6$ alkyl group, a phenyl group or a benzyl group; $R^{10}$ represents, for example, a $C_1$-$C_6$ alkyl group, a phenyl group or a benzyl group; "Pro" represents protecting group of carboxyl group; and X represents a halogen atom.

Production Process 1

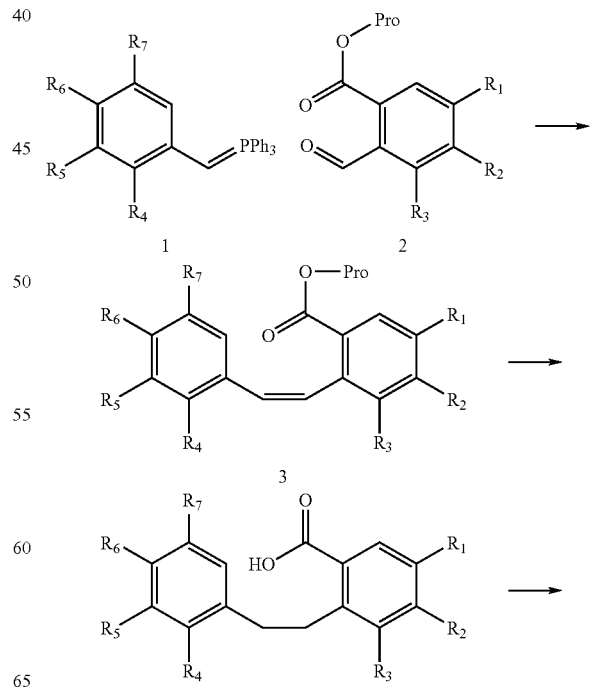

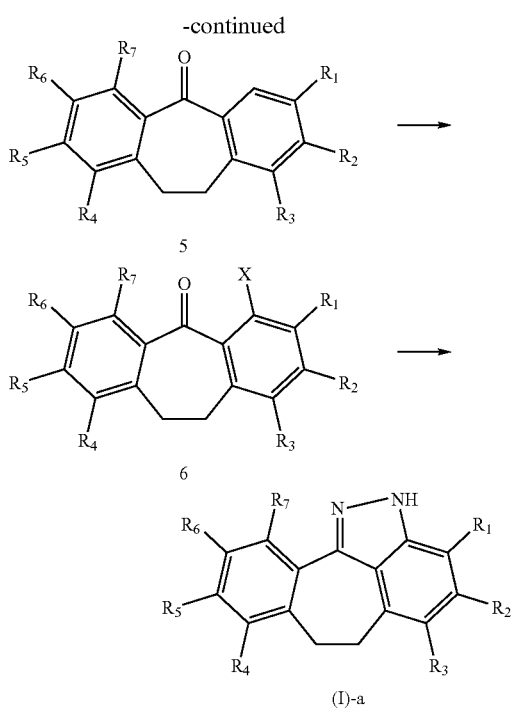

The compound (1)-a can be produced by subjecting the phosphonylide 1 and the aldehyde 2 to a Wittig reaction, reducing the olefin, deprotecting the protecting group to thereby yield the compound 4, closing the ring by a Friedel-Crafts reaction to thereby yield the ketone 5, halogenating the ortho position of the ketone, and closing the ring with hydrazine.

A typical process for preparing the compound 3 is a Wittig reaction between the aldehyde 2 and the phosphonylide 1. The base used for preparing the phosphonylide 1 from a phosphonium salt includes, but is not limited to, sodium hydride, sodium hydrogencarbonate, potassium carbonate, sodium hydroxide, potassium tert-butoxide, and benzyltrimethylammonium hydroxide. The base is generally used in an amount from 1 equivalent to 2 equivalents. The solvents for use herein are not specifically limited, as long as they are inert to the reaction, and include, for example, ether solvents such as diethyl ether, tetrahydrofuran, dioxane or dimethoxyethane, halogenated hydrocarbons such as dichloromethane or chloroform, as well as ethyl acetate, acetonitrile, toluene, dimethyl sulfoxide, and dimethylformamide. The reaction temperature is generally from 0° C. to room temperature.

The compound 4 can be produced by hydrogenating the olefin 3 and then deprotecting the ester. The ester-protecting group is not specifically limited, as long as it can endure the Wittig reaction, and a substituent that can be deprotected concurrently in the hydrogenation is convenient. Preferred examples of the protecting group satisfying such a requirement are benzyl group and benzyloxymethyl group. A catalyst for hydrogenating the olefin of the compound 3 is not specifically limited and includes, for example, palladium-carbon, rhodium-carbon, platinum oxide, and palladium hydroxide-carbon. The pressure of hydrogen is from 1 to 5 atm. The solvents for use herein are not specifically limited, as long as they are inert to the reaction, and include, for example, ether solvents such as diethyl ether, tetrahydrofuran, dioxane or dimethoxyethane, halogenated hydrocarbons such as dichloromethane or chloroform, as well as acetic acid, ethyl acetate, acetonitrile, toluene, and dimethylformamide. The reaction temperature is generally from room temperature to the reflux temperature of the solvent.

The Friedel-Crafts reaction of the compound 4 can be performed by allowing, for example, polyphosphoric acid, diphosphorus pentaoxide or sulfuric acid to act directly upon the compound 4 or by converting the compound 4 into an acid chloride and then treating the acid chloride with a Lewis acid to thereby yield the closed circular compound 5. When the ring of the compound 4 is directly closed, the aforementioned reagent is generally used as a solvent, and the reaction temperature is generally room temperature or higher. Reagent for converting into the acid chloride include, for example, thionyl chloride, oxalyl chloride, sulfuryl chloride, and phosphorus pentaoxide. The reagent is generally used in an amount from 1 equivalent to the solvent amount. The reaction can be performed in the absence of, or in the presence of, a solvent. Such solvents are not specifically limited, as long as they are inert to the reaction, and include, for example, ether solvents such as diethyl ether, tetrahydrofuran, dioxane or dimethoxyethane, halogenated hydrocarbons such as dichloromethane or chloroform, as well as hydrocarbon solvents such as benzene or toluene. It is also acceptable that a catalytic amount of dimethylformamide is added to thereby proceed the reaction smoothly. The reaction temperature is generally from 0° C. to the reflux temperature. The Lewis acid for closing the ring of the acid chloride includes, for example, aluminum chloride, antimony pentachloride, iron chloride, and titanium tetrachloride. It is generally used in an amount of 1 equivalent or more. The solvents for use herein are not specifically limited, as long as they are inert to the reaction, and preferred examples include nitrobenzene, carbon disulfide, dichloromethane, and carbon tetrachloride. The reaction temperature is generally from ice-cooling temperature to the reflux temperature of the solvent.

The compound 6 can be produced by allowing the compound 5 to react with thallium trifluoroacetate and potassium iodide according to the method disclosed in Tetrahedron Lett., 1979, 591-592. As another reagent for halogenation, iodobenzene diacetate, mercury trifluoroacetate or the like may be used.

The compound (1)-a can be produced by cyclizing the compound 6 with hydrazine monohydrate. The reaction can be performed in a solvent amount of hydrazine or in a solvent. The solvent is not specifically limited, as long as it is inert to the reaction, and includes, for example, ether solvents such as diethyl ether, tetrahydrofuran, dioxane or dimethoxyethane, alcohol solvents such as methanol, ethanol or propanol, as well as dimethyl sulfoxide, benzene, toluene, and pyridine. These solvents can be used alone or in combination as a mixture. The amount of hydrazine monohydrate is 2 equivalents or more to the raw material. The reaction temperature is generally from 0° C. to the reflux temperature of the solvent.

Production Process 2

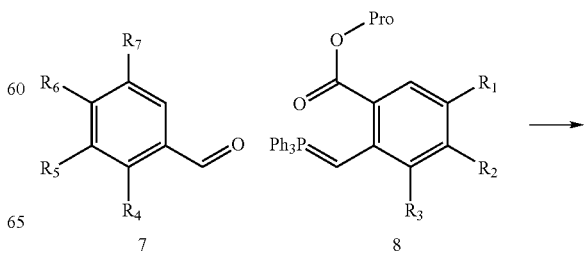

-continued

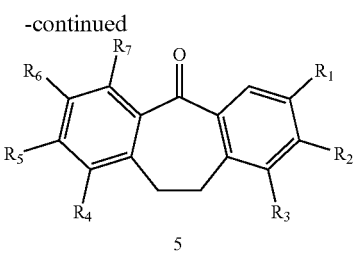

5

The compound 5 can also be produced by subjecting the aldehyde 7 and the phosphonylide 8 to a Wittig reaction, reducing the olefin, and subjecting to a Friedel-Crafts reaction as in Production Process 1.

Production Process 3

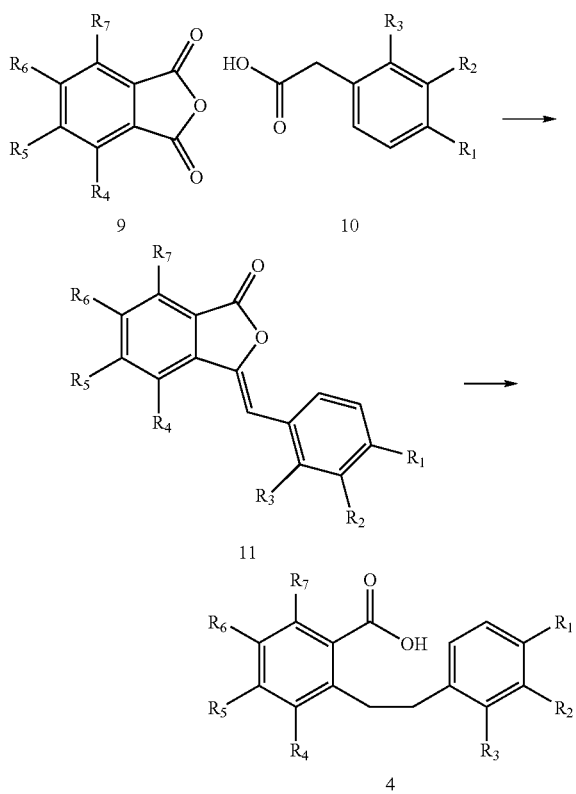

The compound 4 can also be produced by the procedure of Production Process 3. The compound 11 can be synthesized by condensing phthalic anhydride with an equivalent amount of phenylacetic acid in the presence of a base. The compound 4 can be produced by subjecting the compound 11 to reduction such as catalytic reduction.

In the condensation, phenylacetic acid is generally used in an amount of 1 equivalent to 2 equivalents to phthalic anhydride. The base includes, for example, sodium acetate, potassium acetate, potassium carbonate, and potassium tert-butoxide. The amount is from a catalytic amount to 1 equivalent to the raw material. The compounds are fused in the absence of, or in the presence of a solvent. The solvent is not specifically limited, as long as it is inert to the reaction, and includes, for example, benzene, toluene, pyridine, and collidine. These solvents can be used alone or in combination as a mixture. The reaction temperature is from 100° C. to the reflux temperature.

The reduction of the compound 11 can also be performed by a classical reduction procedure with hydroiodic acid and red phosphorus in combination, as well as catalytic reduction. Catalysts for catalytic reduction are not specifically limited and include, for example, palladium-carbon, rhodium-carbon, platinum oxide, and palladium hydroxide-carbon. The pressure of hydrogen is from 1 to 5 atm. The solvents for use herein are not specifically limited, as long as they are inert to the reaction, and include, for example, ether solvents such as diethyl ether, tetrahydrofuran, dioxane or dimethoxyethane, halogenated hydrocarbons such as dichloromethane or chloroform, as well as acetic acid, ethyl acetate, acetonitrile, toluene, and dimethylformamide. The reaction temperature is generally from room temperature to the reflux temperature of the solvent.

Production Process 4

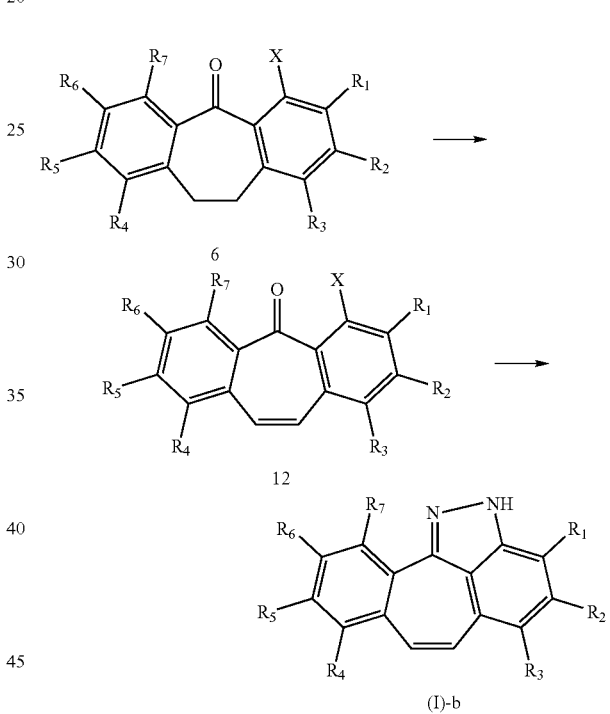

The compound (1)-b can be produced by brominating the compound 6 with N-bromosuccinimide, introducing an olefin moiety by treating with a base to thereby yield the compound 12, and closing the ring with hydrazine. The halogenation of the compound 6 is not specifically limited to bromination, as long as a functional group that can be removed after introduction. The functional group includes, for example, leaving groups such as chloro group or hydroxyl group. Preferred reagents for halogenation include N-halogenated succinimide and bromine. The amount of the reagent is generally from about 1 equivalent to about 2 equivalents. A catalytic amount of 2,2'-azobisisobutyronitrile or benzoyl peroxide as a radical reaction initiator can be in coexistence. The solvents for halogenation are not specifically limited, as long as they are inert to the reaction, and preferred examples include halogen solvents such as carbon tetrachloride, as well as benzene. The reaction temperature is from −78° C. to the reflux temperature of the solvent. The reaction for removing hydrogen halide moiety to thereby yield the olefin 12 can be generally performed by action of a base. Preferred examples of the base include triethylamine, Hunig's base, diazabicycloundecene and pyridine. The amount of the base is not specifically limited, as long as it is 1 equivalent or more, and can be a solvent amount. The reaction temperature is from −78° C. to the reflux temperature of the solvent.

The compound (1)-b can be produced by cyclizing the compound 12 with hydrazine by the cyclization procedure of the compound 6.

Production Process 5

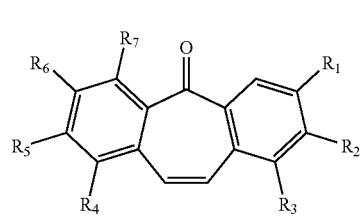
13

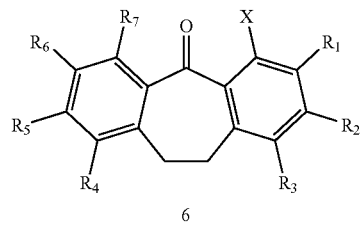
12

Alternatively, the compound 12 can also be produced by halogenating the compound 13. The compound 12 can be synthesized according to the halogenation procedure of the compound 5.

Production Process 6

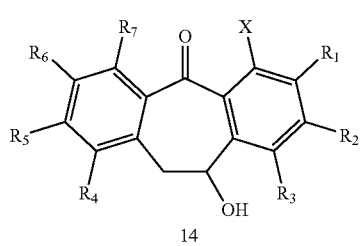
6

14

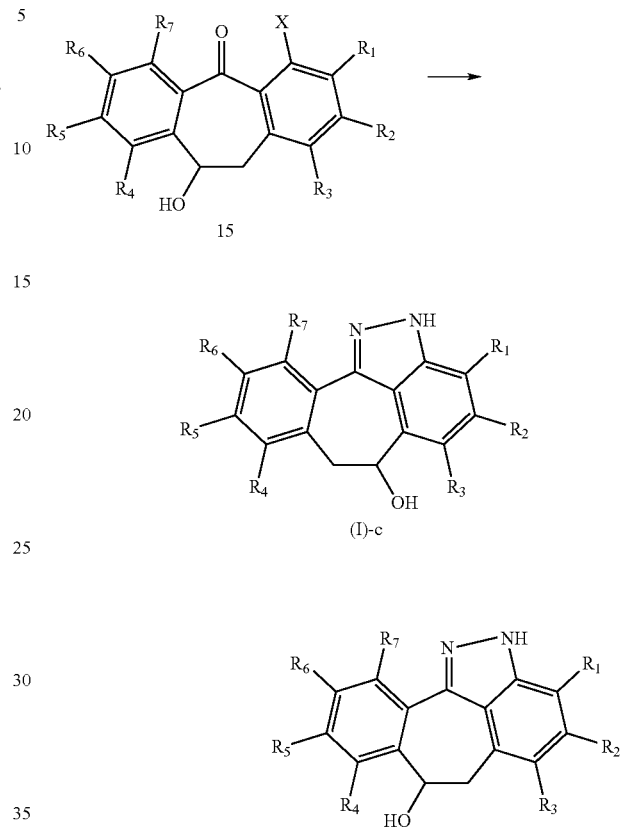

The compounds (1)-c and (1)-d can be produced by brominating the compound 6 with N-bromosuccinimide, introducing a hydroxyl group to thereby yield the compounds 14 and 15, and closing the rings with hydrazine. The hydroxyl group can be introduced by brominating the compound 6 according to the procedure of Production Process 4, allowing the brominated compound to react with sodium acetate to thereby yield an acetate derivative, and hydrolyzing the acetate derivative. The solvents for conversion into the acetate derivative are not specifically limited, as long as they are inert to the reaction, and preferred examples include ether solvents such as tetrahydrofuran or dioxane, as well as dimethyl sulfoxide. The amount of sodium acetate is from 1 to 2 equivalents. The reaction temperature is from −78° C. to the reflux temperature of the solvent. The hydrolysis reaction of the acetate is preferably performed by using 1 to 3 equivalents of a base such as aqueous sodium hydroxide solution or aqueous potassium hydroxide solution in an alcohol solvent such as methanol or ethanol, or in an ether solvent such as tetrahydrofuran or dioxane. The reaction temperature is from ice-cooling temperature to the reflux temperature of the solvent. The acetate derivative can also be deacetated by allowing the acetate derivative to react with hydrazine directly. The ring cyclization of the compounds 14 and 15 can be closed with hydrazine by the procedure of Production Process 1.

Production Process 7

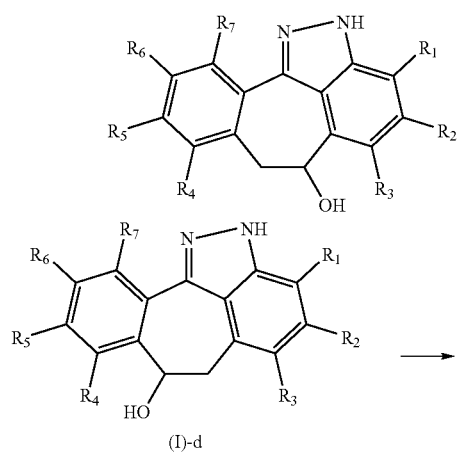

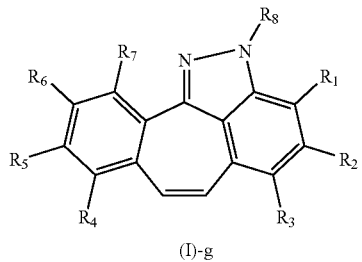

The compound (1)-g can be produced by allowing the compound 6 to react with an alkyl hydrazine. The ring cyclization can be closed with the alkyl hydrazine by the procedure of Production Process 1.

Production Process 9

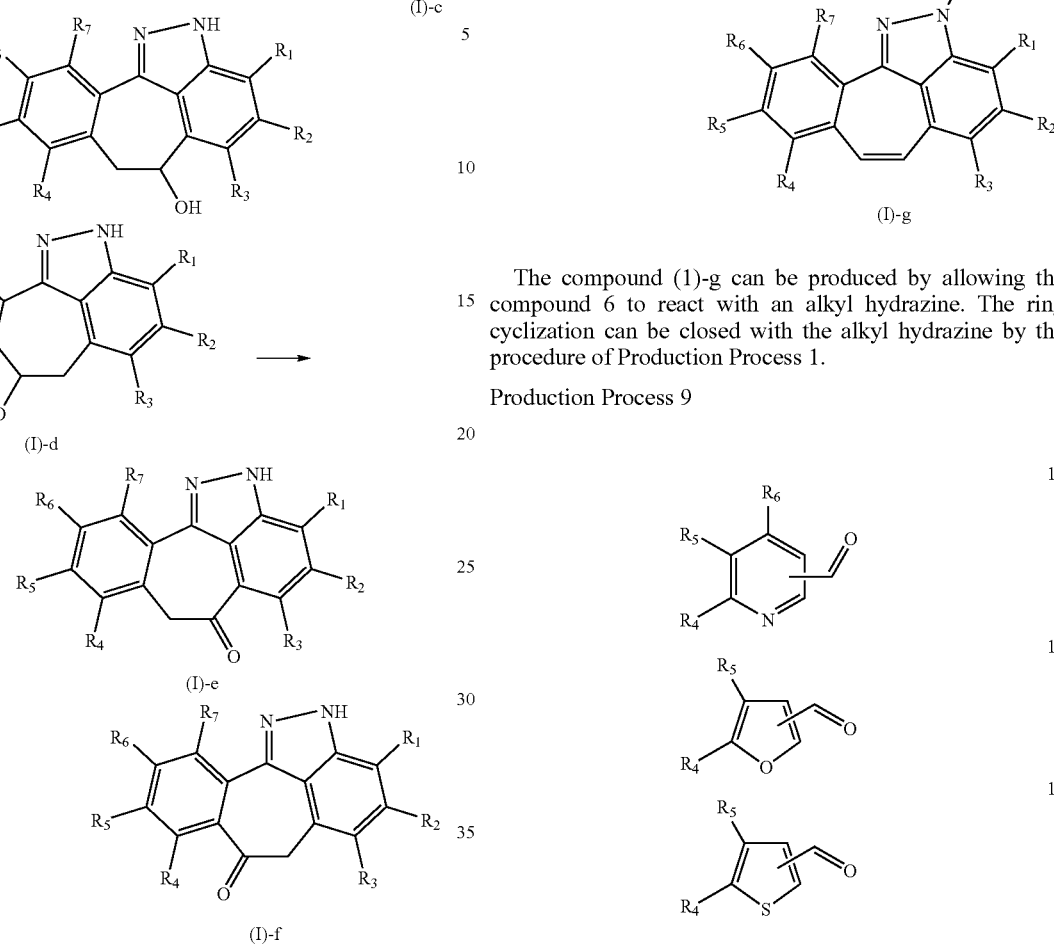

The compounds (1)-e and (1)-f can be produced by oxidizing the compounds (1)-c and (1)-d. Oxidizing agents for use herein include, for example, manganese dioxide, sulfur trioxide-pyridine complex, and various chromic acid oxidizing agents. The oxidation can also be performed by Swern oxidation or Moffatt oxidation. The solvents for use herein can be any solvents that are not involved in the reaction and include, for example, halogenated hydrocarbons such as dichloromethane or chloroform, as well as ethyl acetate, acetonitrile, dimethyl sulfoxide, and dimethylformamide. The reaction temperature is generally from −78° C. to the reflux temperature of the solvent.

Production Process 8

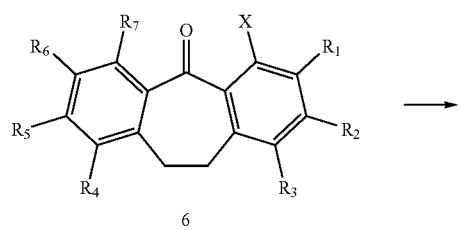

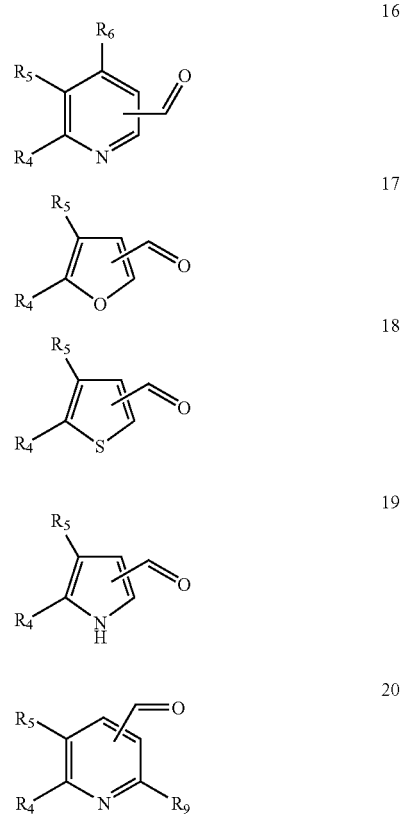

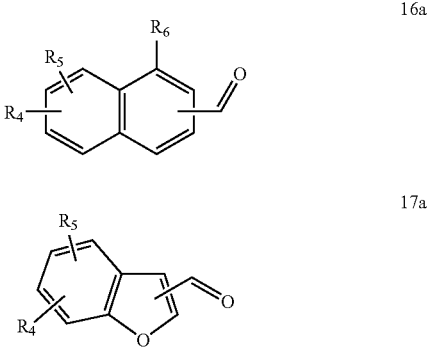

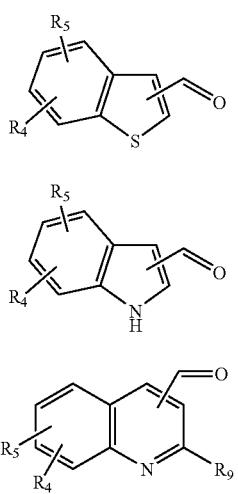

A variety of the compounds (1) can be synthesized according to the procedures of Production Processes 1 to 8 using, instead of the compound 7, the aldehyde 16, 17, 18, 19, 20, 16a, 17a, 18a, 19a or 20a.

Production Process 10

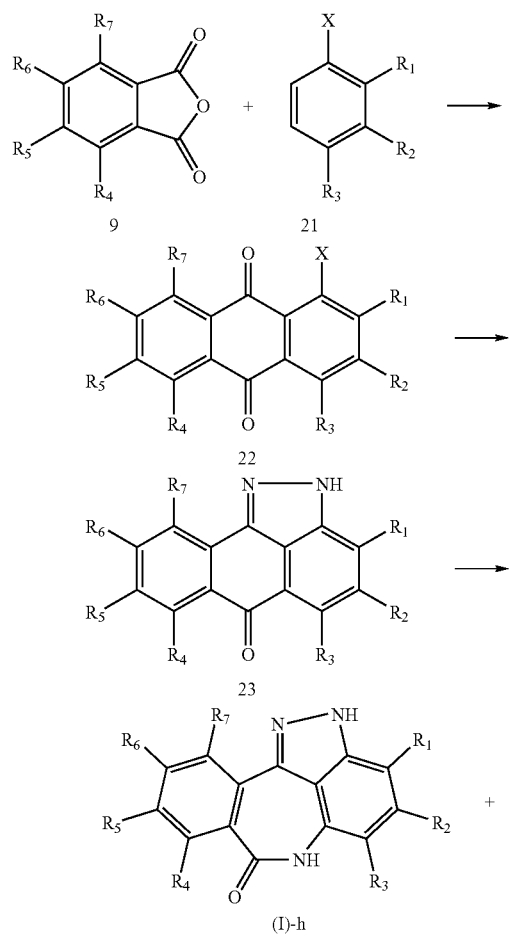

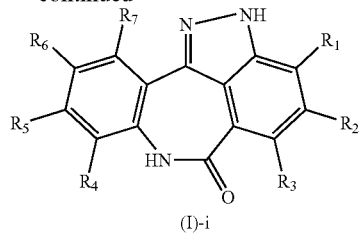

The compounds (1)-h and (1)-i can be produced by performing a Friedel-Crafts reaction two times to thereby yield the quinone 22, closing the ring with hydrazine to thereby yield the compound 23, and converting the compound 23 into a lactam by a Schmidt rearrangement reaction. The first Friedel-Crafts reaction is performed in the presence of aluminum trichloride in an amount of 2 to 3 equivalents. The solvents for use herein are preferably halogenated solvents such as dichloromethane or chloroform, but the reaction can also be performed in the absence of the solvent. The reaction temperature is from ice-cooling temperature to the reflux temperature of the solvent. The second Friedel-Crafts reaction can be performed by heating in polyphosphoric acid or concentrated sulfuric acid. The reaction temperature is from 50° C. to 120° C. The ring of the compound 22 can be closed with hydrazine by the procedure of Production Process 1. The compound 23 can be converted into the lactam by allowing the compound 23 to react with 2 to 6 equivalents of sodium azide in polyphosphoric acid or concentrated sulfuric acid. The reaction temperature is from ice-cooling temperature to the room temperature.

Production Process 11

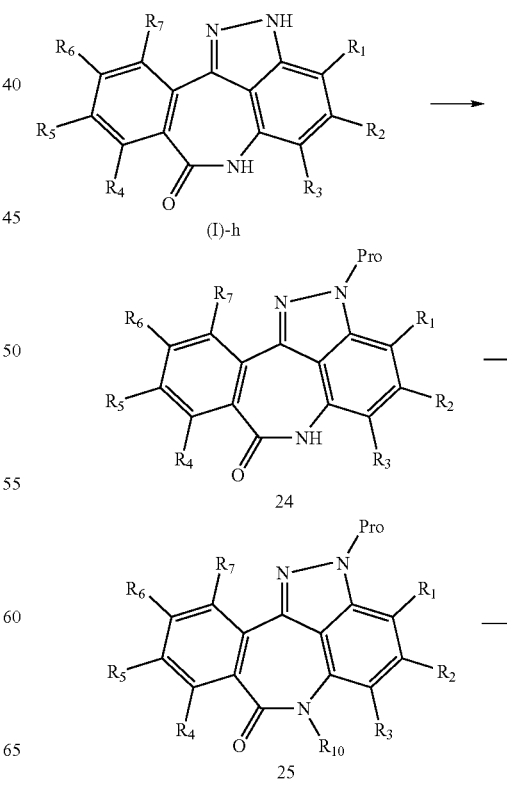

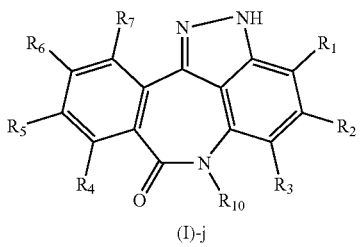

(I)-j

The compound (1)-j can be produced by protecting the pyrazole moiety of the lactam (1)-h, alkylating the lactam to yield the compound 25, and deprotecting the compound 25.

Protecting groups for introducing into the pyrazole moiety include, for example, tert-butyloxycarbonyl group, p-toluenesulfonyl group, and triphenylmethyl group. The tert-butyloxycarbonyl group or p-toluenesulfonyl group can be introduced by allowing the compound (1)-h to react with di-tert-butyl dicarbonate or p-toluenesulfonyl chloride in the presence of a base. Such bases are not specifically limited but preferred examples are triethylamine and 4-N,N-dimethylaminopyridine. The solvents for use herein are not specifically limited, as long as they are inert to the reaction and include, for example, ether solvents such as tetrahydrofuran or dioxane, halogenated hydrocarbons such as dichloromethane or chloroform, as well as ethyl acetate, acetonitrile, dimethyl sulfoxide, and dimethylformamide. The reaction temperature is generally from 0° C. to the reflux temperature of the solvent. The triphenylmethyl group can be introduced by allowing the compound (1)-h to react with chlorotriphenylmethane in the presence of a base. Such bases are not specifically limited, but preferred examples are sodium hydride, potassium tert-butoxide, lithium diisopropylamide, potassium carbonate, and sodium hydroxide. The solvents for use herein are not specifically limited, as long as they are inert to the reaction and include, for example, ether solvents such as tetrahydrofuran or dioxane, as well as dimethyl sulfoxide and dimethylformamide. The reaction temperature is from −20° C. to the reflux temperature of the solvent.

The compound 24 can be alkylated by allowing the compound 24 to react with an alkyl halide in the presence of a base. Where necessary, sodium iodide can be added. Such bases are not specifically limited but preferred examples are sodium hydride, potassium tert-butoxide, lithium diisopropylamide, potassium carbonate, and sodium hydroxide. Solvents for use herein are not specifically limited, as long as they are inert to the reaction and include, for example, ether solvents such as tetrahydrofuran or dioxane, as well as dimethyl sulfoxide and dimethylformamide. The reaction temperature is from −20° C. to the reflux temperature of the solvent.

The tert-butyloxycarbonyl group and triphenylmethyl group can be easily removed from the compound 25 by using an acid. Such acids include, for example, hydrochloric acid, sulfuric acid, and trifluoroacetic acid. Where necessary, a radical scavenger such as thiophenol or tri-iso-propylsilane can be added. The solvents for use herein are not specifically limited, as long as they are inert to the reaction and include, for example, halogenated hydrocarbons such as dichloromethane or chloroform, and alcohol solvents such as methanol or ethanol. The reaction temperature is from −20° C. to the reflux temperature of the solvent. The tert-butyloxycarbonyl group and p-toluenesulfonyl group can be easily removed by using a base. Such bases include, but are not specifically limited to, aqueous sodium hydroxide and aqueous potassium hydroxide. The solvents for use herein are not specifically limited, as long as they are inert to the reaction, and include, for example, alcohol solvents such as methanol or ethanol, and ether solvents such as tetrahydrofuran or dioxane. The reaction temperature is from room temperature to the reflux temperature of the solvent.

Production Process 12

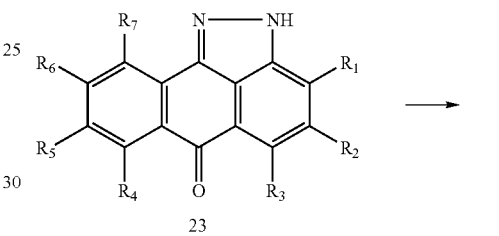

23

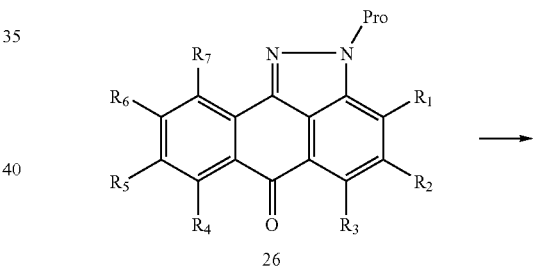

26

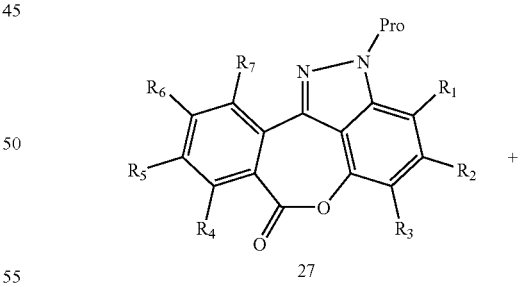

27

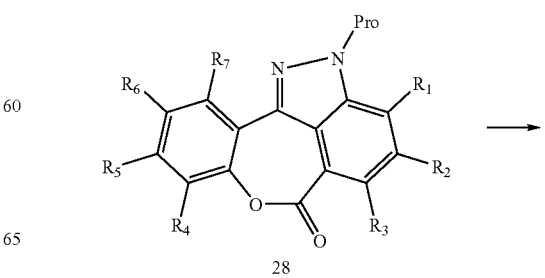

28

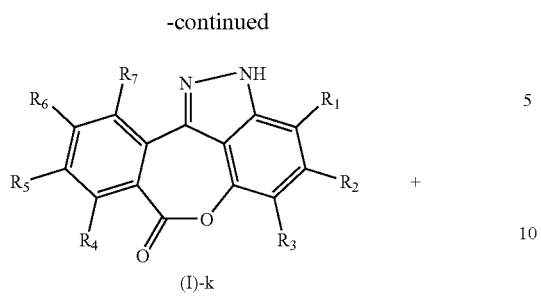

(I)-k

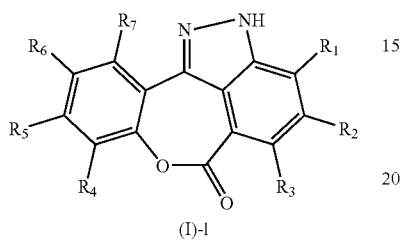

(I)-l

The compounds (1)-k and (1)-i can be produced by protecting the pyrazole moiety of the compound 23, subjecting the resulting compound to Baeyer-Villiger reaction to yield the lactones 27 and 28, and removing the protecting group.

The protecting group can be introduced into the pyrazole moiety by the procedure of Production Process 11. The compound 26 can be converted into the lactones by allowing the compound 26 to react with a peracid in a halogenated hydrocarbon solvent such as dichloromethane or chloroform. Such peracids include, for example, perbenzoic acid, m-chloroperbenzoic acid, peracetic acid, and trifluoroperacetic acid. The amount of peracid is from 1 to 2 equivalents. The reaction temperature is from ice-cooling temperature to the reflux temperature of the solvent. The compounds 27 and 28 are deprotected by the procedure of Production Process 11.

Production Process 13

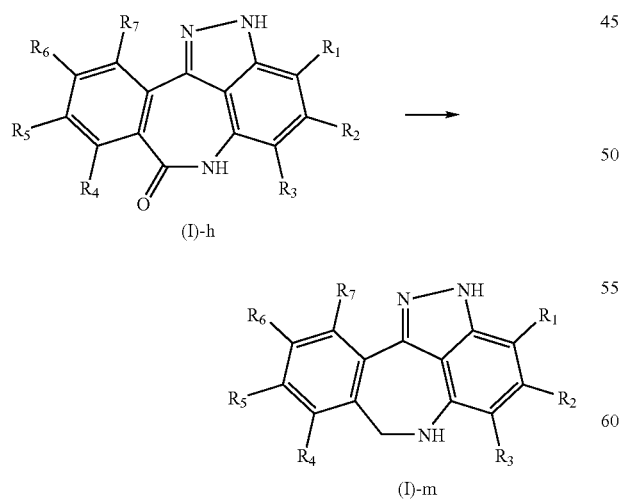

The compound (1)-m can be produced by reducing the lactam (1)-h. Reducing agents for use herein include, for example, lithium aluminum hydride, diborane, borane-tetrahydrofuran complex, and borane-methyl sulfide complex. The solvents for use herein are not specifically limited, as long as they do not adversely affect the reaction, but preferred examples are ether solvents such as tetrahydrofuran or dioxane. The amount of the reducing agent is from 1 to 5 equivalents. The reaction temperature is from ice-cooling temperature to the reflux temperature of the solvent.

Production Process 14

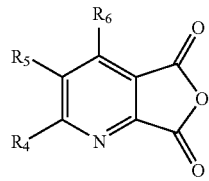

29

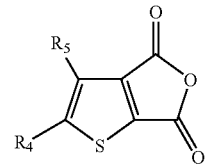

30

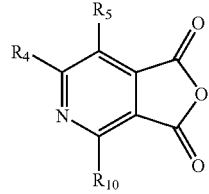

31

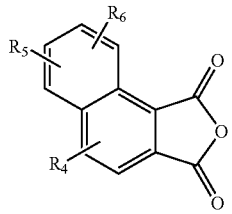

29a

29b

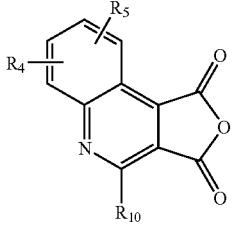

31a

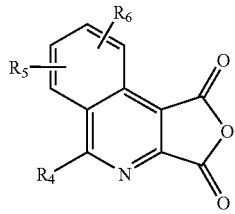

29c

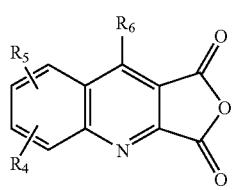

29d

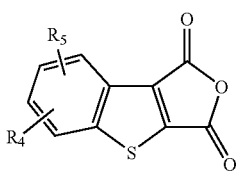

30a

A variety of compounds (1) can be synthesized by the procedures of Production Processes 10 to 13 using, instead of the compound 9, the above-mentioned acid anhydride 29, 30, 31, 29a, 29b, 29c, 29d, 30a or 31a.

Production Process 15

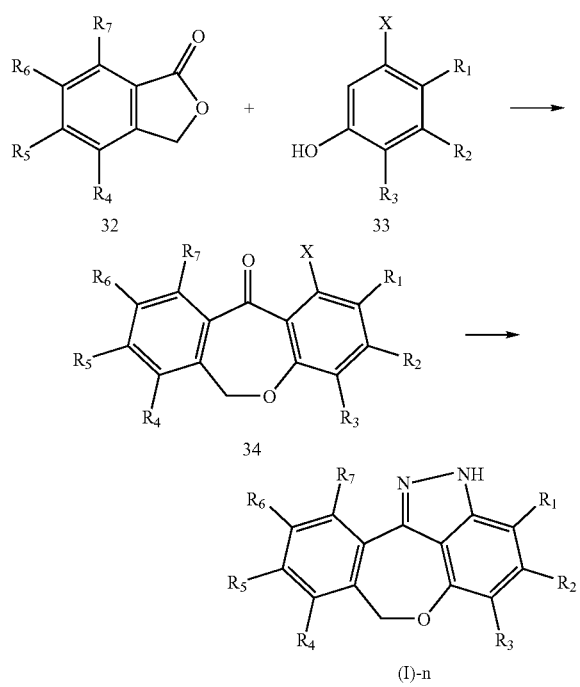

The compound (1)-n can be produced by opening the ring of the lactone 32 with the phenol 33, closing the ring by a Friedel-Crafts reaction to yield the compound 34, and further closing the ring of the compound 34 with hydrazine. The reaction between the lactone 32 and the phenol 33 is performed in the presence of a base. Such bases are not specifically limited but preferred examples are sodium hydride, potassium tert-butoxide, sodium methoxide, lithium diisopropylamide, and potassium carbonate. The solvents for use herein are not specifically limited, as long as they are inert to the reaction, and include, for example, ether solvents such as tetrahydrofuran or dioxane, as well as dimethyl sulfoxide and dimethylformamide. The reaction temperature is from −20° C. to the reflux temperature of the solvent. The resulting carboxylic acid derivative can be cyclized by allowing the derivative to react with trifluoroacetic anhydride in a halogenated hydrocarbon solvent such as dichloromethane or chloroform. Where necessary, boron trifluoride-etherate can be added. The reaction temperature is from ice-cooling temperature to the reflux temperature of the solvent. The ring can also be closed by heating in polyphosphoric acid. The ring cyclization of the compound 34 can be closed with hydrazine by the procedure of Production Process 1.

Production Process 16

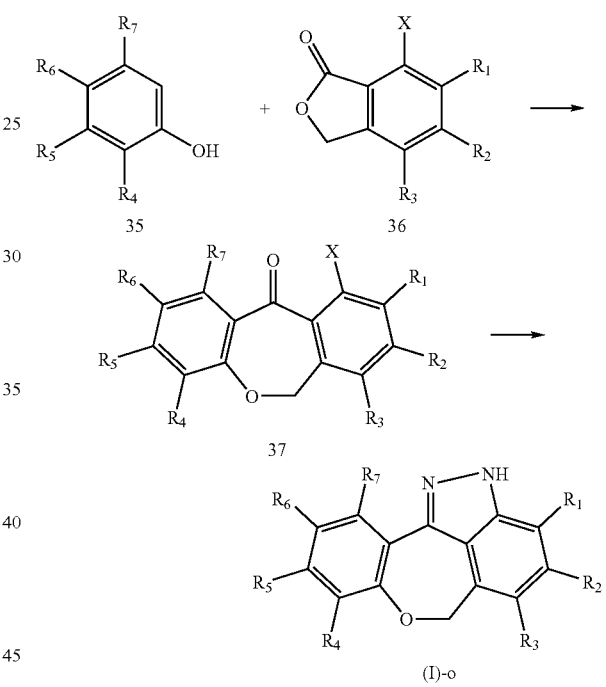

The compound (1)-o can be produced by allowing the phenol 35 to react with the lactone 36 by the procedure of Production Process 15.

Material compounds for use in the production of the compounds of the present invention can be in the form of salts and/or hydrates and are not specifically limited as long as they do not adversely affect the reactions. When the compounds (I) according to the present invention are obtained as free compounds, they can be converted into acceptable salts of the above-mentioned compound (I) according to a conventional procedure. Various isomers such as geometrical isomers, optical isomers due to an asymmetric carbon, stereoisomers, and tautomers obtained as the compounds (I) according to the present invention can be purified and isolated according to a conventional separation means. Such separation means include, for example, recrystallization, diastereomeric salt method, enzymatic resolution, and a variety of chromatography such as thin layer chromatography, column chromatography or gas chromatography.

The term "salt(s)" as used in the present description means and includes, for example, salts with inorganic acids, salts with organic acids, salts with inorganic bases, salts with organic bases, and salts with acidic or basic amino acids. Among them, pharmacologically acceptable salts are preferred.

Preferred examples of the salts with inorganic acids are salts with hydrochloric acid, hydrobromic acid, sulfuric acid, nitric acid or phosphoric acid. Preferred examples of the salts with organic acids are salts with acetic acid, succinic acid, fumaric acid, maleic acid, tartaric acid, citric acid, lactic acid, stearic acid, benzoic acid, methanesulfonic acid or p-toluenesulfonic acid.

Preferred examples of the salts with inorganic bases are alkali metal salts such as sodium salts or potassium salts, alkaline earth metal salts such as calcium salts or magnesium salts, as well as aluminum salts and ammonium salts. Preferred examples of the salts with organic bases are salts of diethylamine, diethanolamine, meglumine or N,N'-dibenzylethylenediamine.

Preferred examples of the salts with acidic amino acids are salts with aspartic acid or glutamic acid. Preferred examples of the salts with basic amino acids are salts with arginine, lysine or ornithine.

The compounds represented by the formula (I) according to the present invention, a salt thereof or a hydrate of them can be formulated into pharmaceutical preparations according to a conventional procedure. Preferred dosage forms are tablets, powders, fine granules, granules, coated tablets, capsules, syrups, troches, inhalants, suppositories, injections, ointments, ophthalmic ointments, eye drops, nasal drops, ear drops, cataplasms, and lotions. In the formulation, generally used fillers, binders, disintegrators, lubricants, coloring agents, and flavoring agents, as well as stabilizers, emulsifiers, absorbefacients, surfactants, pH adjusting agents, antiseptics, and antioxidants according to necessity can be used. They can be formulated according to a conventional procedure using components generally used as raw materials for pharmaceutical preparations. Examples of such components include (1) animal or vegetable oils such as soybean oil, beef tallow or synthetic glycerides; (2) hydrocarbons such as liquid paraffins, squalane or solid paraffins; (3) ester oils such as octyldodecyl myristate or isopropyl myristate; (4) higher alcohols such as cetostearyl alcohol or behenyl alcohol; (5) silicon resins; (6) silicon oils; (7) surfactants such as polyoxyethylene fatty acid esters, sorbitan fatty acid esters, glycerin fatty acid esters, polyoxyethylene sorbitan fatty acid esters, polyoxyethylene hydrogenated castor oils or polyoxyethylene-polyoxypropylene block copolymers; (8) water-soluble polymers such as hydroxyethyl cellulose, poly(acrylic acid)s, carboxyvinyl polymers, polyethylene glycol, polyvinylpyrrolidone or methylcellulose; (9) lower alcohols such as ethanol or isopropanol; (10) polyhydric alcohols such as glycerol, propylene glycol, dipropylene glycol or sorbitol; (11) sugars such as glucose or sucrose; (12) inorganic powders such as silicic anhydride, magnesium aluminium silicate or aluminium silicate; and (13) purified water.

1) The fillers include, for example, lactose, corn starch, sucrose, glucose, mannitol, sorbitol, crystalline cellulose, and silicon dioxide; 2) the binders include, for example, polyvinyl alcohol, polyvinyl ether, methylcellulose, ethylcellulose, gum arabic, gum tragacanth, gelatin, shellac, hydroxypropyl cellulose, hydroxypropylmethyl cellulose, polyvinylpyrrolidone, polypropylene glycol-polyoxyethylene block polymers, meglumine, calcium citrate, dextrin, and pectin; 3) the disintegrators include, for example, starch, agar, gelatin powder, crystalline cellulose, calcium carbonate, sodium hydrogencarbonate, calcium citrate, dextrin, pectin, and carboxymethylcellulose calcium; 4) the lubricants include, for example, magnesium stearate, talc, polyethylene glycol, silica, and hardened vegetable oils; 5) the coloring agents can be any coloring agents which are approved to add to pharmaceutical preparations; 6) the flavoring agents include, for example, cocoa powder, menthol, aromatic powder, peppermint oil, borneol, and cinnamon powder; 7) the antioxidants can be any antioxidants which are approved to add to pharmaceutical preparations such as ascorbic acid or α-tocopherol.

1) As oral preparations, the compound according to the present invention or the salt thereof is compounded with a filler, and if necessary, a binder, disintegrator, lubricant, coloring agent, flavoring agent, and other components, and the resulting mixture is formulated according to a conventional procedure into a powder, fine granules, granules, tablet, coated tablet, capsule, etc. 2) The tablets and granules can be appropriately coated with, for example, sugar or gelatin, or other according to necessity. 3) Liquid formulations such as syrups, injection preparations or eye droppers can be prepared in a conventional method, by adding a pH adjusting agents, solubilizer, and isotonizing agent, and if necessary, a solubilizing agent, stabilizer, buffer, suspending agent, antioxidant, and other components. The liquid formulations can also be formed into freeze-dried products. The injections can be administered intravenously, subcutaneously and/or intramuscularly. Preferred examples of the suspending agents are methylcellulose, polysorbate 80, hydroxyethyl cellulose, gum arabic, tragacanth powder, sodium carboxymethylcellulose, and polyoxyethylene sorbitan monolaurate; preferred examples of solubilizers are polyoxyethylene hardened caster oil, polysorbate 80, nicotinamide, and polyoxyethylene sorbitan monolaurate; preferred examples of the stabilizers are sodium sulfite, sodium metasulfite, and ether; preferred examples of the preservatives are methyl p-hydroxybenzoate, ethyl p-hydroxybenzoate, sorbic acid, phenol, cresol, and chlorocresol. 4) External preparations can be produced according to a conventional procedure not specifically limited. Base materials for use herein can be any raw materials generally used in, for example, pharmaceutical preparations, quasi drugs, and cosmetics. Such raw materials include, for example, animal or vegetable oils, mineral oils, ester oils, waxes, higher alcohols, fatty acids, silicon oils, surfactants, phospholipids, alcohols, polyhydric alcohols, water-soluble polymers, clay minerals, and purified water. If necessary, any of pH adjusting agents, antioxidants, chelating agents, antiseptics and antimolds, coloring agents, and flavors can be added. In addition, components having differentiation-inducing action, blood-flow accelerators, bactericides, anti-inflammatory agents, cell activators, vitamins, amino acids, humectants, keratolytic agents, and other components can be added according to necessity.

The dose of the pharmaceutical preparation according to the present invention varies depending on the degree of symptom, age, sex, body weight, administration mode, type of the salt, difference in sensibility to the drug, concrete type of the disease, and other factors. Generally, in oral administration, the pharmaceutical preparations may be administered at a daily dose of about 30 µg to about 1000 mg, preferably about 100 µg to about 500 mg, and more preferably about 100 µg to about 100 mg for an adult in one to several divided doses. In injection administration, they may be administered at a daily dose of about 1 to about 3000 µg/kg, and preferably about 3 to about 1000 µg/kg for an adult in one to several divided doses.

The present invention can provide novel fused indazole compounds. The compounds (I) according to the present invention or the salts thereof have excellent inhibitory action on c-Jun amino-terminal kinases, especially on JNK 3. Accordingly, the compounds (I) according to the present invention or the salts thereof, and pharmaceutical compositions containing the same are useful as therapeutic agents or prophylactic agents for an immunologic disease, inflammatory disease and/or neurodegenerative disease. They are particularly useful as an agent for treating or preventing, for example, neurodegenerative diseases such as Alzheimer's disease, Parkinson's disease, Huntington's chorea or multiple sclerosis, amyotrophic lateral sclerosis, ischemic diseases, brain disorder in cerebral stroke, schizophrenia, depression, epilepsy, various immunologic diseases or inflammatory diseases.

EXAMPLES

The following production examples, examples and test examples are indicated by illustration, and the compounds according to the present invention are never restricted by the following examples. Those skilled in the art can modify not only the following examples but also the claims according to the present description in various ways to exert the most of the present invention, and such modifications and variations are also included within the scope of the appended claims relating to the present description.

Example 1-a

2-[2-Ethoxycarbonyl]phenethyl]benzoic acid 30.3 g of ethyl 2-[(1,1,1-triphenylphosphino)methyl]benzoate bromide was suspended in 150 ml of dry N,N-dimethylformamide and 2.8 g of sodium hydride (60% in oil) was added under ice-cooling, followed by stirring for 20 minutes. To the reaction mixture was added dropwise a solution of 24 g of benzyl 2-formylbenzoate in 30 ml dry N,N-dimethylformamide, followed by stirring for 1 hour. After warming the reaction mixture to room temperature, water was added and the mixture was extracted with ethyl acetate for two times. The organic layer was washed with water, dried over anhydrous magnesium sulfate, the solvent was evaporated, and the residue was purified and separated by silica gel column chromatography (ethyl acetate:hexane=1:15). 24.0 g of the resulting benzyl [2-[2-(ethoxycarbonyl)phenyl]-1-ethenyl]benzoate was dissolved in 150 ml of ethanol and 1.0 g of platinum oxide was added, followed by stirring in hydrogen gas under atmospheric pressure for 3 hours. The reaction mixture was filtered through Celite and the solvent was evaporated, to give 17 g of the title compound as a colorless powder.

$^1$H-NMR (400 MHz, CDCl$_3$); δ (ppm) 1.38 (3H, t, J=6.3 Hz), 3.25-3.38 (4H, m ), 4.37 (2H, q, J=6.3 Hz), 7.25 (1H, t, J=7.8 Hz), 7.25-7.33 (3H, m ), 7.38 (1H, t, J=7.8 Hz), 7.46 (1H, t, J=7.8 Hz), 7.88 (1H, d, J=7.8 Hz), 8.04 (1H, d, J=7.8 Hz).

Example 1-b

Ethyl 5-oxo-10,11-dihydro-5H-dibenzo[a,d]cyclo-heptene-1-carboxylate 17 g of 2-[2-(ethoxycarbonyl)]phenethyl]benzoic acid prepared in Example 1-a was suspended in 100 ml of polyphosphoric acid, followed by heating at 130° C. in an atmosphere of nitrogen gas for 6 hours. After cooling the reaction mixture to room temperature, diluted hydrochloric acid was added and the mixture was extracted with ethyl acetate. The organic layer was washed with water, dried over anhydrous magnesium sulfate, and the solvent was evaporated. The resulting crude product was dissolved in 100 ml of N,N-dimethylformamide, and 9.7 g of potassium carbonate and 5.6 ml of iodoethane were added, followed by stirring at room temperature for 1 hour. Water was added to the reaction mixture and the mixture was extracted with ethyl acetate for two times. The organic layer was washed with water, dried over anhydrous magnesium sulfate, and the solvent was evaporated. The residue was purified and separated by silica gel column chromatography (ethyl acetate:hexane=1:15), to give 13.2 g of the title compound as a colorless oil.

$^1$H-NMR (400 MHz, CDCl$_3$); δ (ppm) 1.42 (3H, t, J=6.3 Hz), 3.27-3.33 (2H, m), 3.46-3.52 (2H, m), 4.40 (2H, q, J=6.3 Hz), 7.24 (1H, d, J=7.7 Hz), 7.32 (1H, t, J=7.7 Hz), 7.34 (1H, t, J=7.7 Hz), 7.45 (1H, t, J=7.7 Hz), 7.83 (1H, d, J=7.7 Hz), 7.90 (1H, d, J=7.7 Hz), 7.98 (1H, d, J=7.7 Hz).

Example 1-c 1-(Hydroxymethyl)-10,11-dihydro-5H-dibenzo[a,d]cyclohepten-5-ol 560 mg of ethyl 5-oxo-10,11-dihydro-5H-dibenzo[a,d]cycloheptene-1-carboxylate prepared in Example 1-b was dissolved in 20 ml dry tetrahydrofuran, and 120 mg of lithium aluminum hydride was added under ice-cooling, followed by stirring for 2 hours. To the reaction mixture were successively added 0.1 ml of water, 0.1 ml of 15% potassium hydroxide solution and 0.3 ml of water, followed by stirring at room temperature for 0.5 hour. The reaction mixture was filtered through Celite, washed with ethyl acetate, and the solvent was evaporated, to give 500 mg of the title compound as a colorless oil.

$^1$H-NMR (400 MHz, CDCl$_3$); δ (ppm) 3.15-3.24 (2H, m), 3.36-3.46 (1H, m), 3.46-3.57 (1H, m), 4.73 (2H, d, J=5.6 Hz), 6.11 (1H, d, J=3.0 Hz), 7.11-7.15 (1H, m), 7.17-7.23 (3H, m), 7.30 (1H, bd, J=7.6 Hz), 7.45-7.50 (2H, m).

Example 1-d (5-Hydroxy-10,11-dihydro-5H-dibenzo[a,d]cyclohepten-1-yl)methyl acetate 4.0 g of 1-(hydroxymethyl)-10,11-dihydro-5H-dibenzo[a,d]cyclohepten-5-ol prepared in Example 1-c was dissolved in 20 ml of tetrahydrofuran, and 1.2 ml of pyridine and 1.4 ml of acetic anhydride were added at room temperature, followed by stirring for 3 days. Water was added to the reaction mixture, and the mixture was extracted with ethyl acetate for two times. The organic layer was washed with water, dried over anhydrous magnesium sulfate, and the solvent was evaporated. The residue was purified and separated by silica gel column chromatography (ethyl acetate:hexane=1:9), to give 3.5 g of the title compound as a colorless powder.

$^1$H-NMR (400 MHz, CDCl$_3$); δ (ppm) 2.08 (3H, s), 2.58 (1H, bs), 3.05-3.20 (2H, m), 3.28-3.47 (2H, m), 5.11 (1H, d, J=12.8 Hz), 5.14 (1H, d, J=12.8 Hz), 6.04 (1H, s), 7.09-7.13 (1H, m), 7.15-7.20 (3H, m), 7.26 (1H, bd, J=7.7 Hz), 7.45-7.50 (2H, m).

Example 1-e

[5-(Acetyloxy)-10,11-dihydro-5H-dibenzo[a,d]cyclohepten-1-yl]methyl acetate 1.0 g of the title diacetate as a colorless oil was obtained as a by-product in the aforementioned reaction.

$^1$H-NMR (400 MHz, CDCl$_3$); δ (ppm) 2.08 (3H, s), 2.09 (3H, s), 3.04-3.14 (2H, m), 3.45-3.60 (2H, m), 5.14 (1H, d, J=13.5 Hz), 5.17 (1H, d, J=13.5Hz), 6.98 (1H, s), 7.14-7.26 (4H, m), 7.32 (1H, d, J=7.5Hz), 7.40-7.45 (2H, m).

Example 1-f (5-Oxo-10,11-dihydro-5H-dibenzo[a,d]cyclohepten-1-yl)methyl acetate 3.5 g of (5-hydroxy-10,11-dihydro-5H-dibenzo[a,d]cyclohepten-1-yl)methyl acetate prepared in Example 1-d was dissolved in 50 ml of dichloromethane and 10 g of manganese dioxide was added, followed by stirring at room temperature for 2 days. The reaction mixture was filtered through Celite, and the filtrate was washed with ethyl acetate and the solvent was evaporated, to give 2.7 g of the title compound as a colorless oil.

$^1$H-NMR (400 MHz, CDCl$_3$); δ (ppm) 2.11 (3H, s), 3.17-3.26 (4H, m), 5.20 (2H, s), 7.23 (1H, bd, J=7.5 Hz), 7.31 (1H, t, J=7.5 Hz), 7.32 (1H, dt, J=1.4, 7.5 Hz), 7.44 (1H, dt, J=1.4, 7.5 Hz), 7.51 (1H, dd, J=1.4, 7.5 Hz), 7.81 (1H, dd, J=1.4, 7.5 Hz), 7.92 (1H, dd, J=1.4, 7.5 Hz).

Example 1-g (6-Iodo-5-oxo-10,11-dihydro-5H-dibenzo[a,d]cyclohepten-1-yl)methyl acetate (1-g(1))

(4-Iodo-5-oxo-10,11-dihydro-5H-dibenzo[a,d]cyclohepten-1-yl)methyl acetate (1-g(2))

4.4 g of (5-oxo-10,11-dihydro-5H-dibenzo[a,d]cyclohepten-1-yl)methyl acetate prepared in Example 1-f was dissolved in 30 ml of trifluoroacetic acid, and 5.0 g of thallium trifluoroacetate was added at room temperature in an atmosphere of nitrogen gas. The mixture was stirred at room temperature for 4 hours, followed by stirring at 50° C. for 2 hours. After the starting material disappeared, 3 ml of an aqueous solution of 1.5 g of potassium iodide was added to the reaction mixture and the mixture was stirred at room temperature for 0.5 hour. To the reaction mixture were added ethyl acetate and water, and the mixture was neutralized with sodium hydrogencarbonate and filtered through Celite. The organic layer was washed with water, dried over anhydrous magnesium sulfate, and the solvent was evaporated. The residue was purified and separated by silica gel column chromatography (ethyl acetate:hexane=1:20), to give 4.1 g of a 3:1 mixture of the title compounds as a colorless oil.

(6-Iodo-5-oxo-10,11-dihydro-5H-dibenzo[a,d]cyclohepten-1-yl)methyl acetate (Major Product) (1-g(1))

$^1$H-NMR (400 MHz, CDCl$_3$); δ (ppm) 2.11 (3H, s), 3.13-3.20 (4H, m), 5.11 (2H, s), 7.04 (1H, t, J=7.6 Hz), 7.21 (1H, dd, J=0.9, 7.6 Hz), 7.38 (1H, t, J=7.6 Hz), 7.54 (1H, dd, J=1.7, 7.6 Hz), 7.75 (1H, dd, J=0.9, 7.6 Hz), 7.85 (1H, dd, J=1.7, 7.6 Hz).

(4-Iodo-5-oxo-10,11-dihydro-5H-dibenzo[a,d]cyclohepten-1-yl)methyl acetate (1-g(2))

$^1$H-NMR (400 MHz, CDCl$_3$); δ (ppm) 2.13 (3H, s), 3.14-3.19 (2H, m), 3.20-3.25 (2H, m), 5.16 (2H, s), 7.11 (1H, d, J=7.6 Hz), 7.19 (1H, d, J=7.6 Hz), 7.34 (1H, t, J=7.6 Hz), 7.45 (1H, t, J=7.6 Hz), 7.74 (1H, d, J=7.6 Hz), 7.81 (1H, d, J=7.6 Hz).

Example 1-h 6,7-Dihydro-2H-benzo[6,7]cyclohepta[cd]indazol-8-ylmethanol (1-h(1))

6,7-Dihydro-2H-benzo[6,7]cyclohepta[cd]indazol-5-ylmethanol (1-h(2))

2.1 g of the mixture of (6-iodo-5-oxo-10,11-dihydro-5H-dibenzo[a,d]cyclohepten-1-yl)methyl acetate and (4-iodo-5-oxo-10,11-dihydro-5H-dibenzo[a,d]cyclohepten-1-yl)methyl acetate prepared in Example 1-g was dissolved in a mixed solvent of 5 ml of pyridine and 5 ml of methanol, and 5 ml of hydrazine monohydrate was added, followed by heating under reflux for 3 days. Water was added to the reaction mixture, and the mixture was extracted with ethyl acetate. The organic layer was washed with water, dried over anhydrous magnesium sulfate, and the solvent was evaporated. The residue was purified and separated by silica gel column chromatography (ethyl acetate:hexane=3:7), to give 330 mg and 130 mg of the title compounds as a colorless powder, respectively.

6,7-Dihydro-2H-benzo[6,7]cyclohepta[cd]indazol-8-ylmethanol (Major Product) (1-h(1))

$^1$H-NMR (400 MHz, DMSO-d$_6$); δ (ppm) 3.05-3.15 (4H, m), 4.63 (2H, d, J=5.3 Hz), 5.16 (1H, t, J=5.3 Hz), 6.90 (1H, d, J=7.6 Hz), 7.23 (1H, t, J=7.6 Hz), 7.26 (1H, t, J=7.6 Hz), 7.32 (1H, d, J=7.6 Hz), 7.35 (1H, d, J=7.6 Hz), 8.02 (1H, d, J=7.6 Hz), 13.14 (1H, s).

6,7-Dihydro-2H-benzo[6,7]cyclohepta[cd]indazol-5-ylmethanol (1-h(2))

$^1$H-NMR (400 MHz, DMSO-d$_6$); δ (ppm) 3.05-3.10 (2H, m), 3.10-3.25 (2H, m), 4.58 (2H, d, J=5.3 Hz), 4.97 (1H, t, J=5.3 Hz), 7.24 (1H, t, J=7.6 Hz), 7.27-7.34 (4H, m), 8.07 (1H, d, J=7.6 Hz), 13.10 (1H, s).

Example 2

6,7-Dihydro-2H-benzo[6,7]cyclohepta[cd]indazole-8-carboxaldehyde 210 mg of 6,7-dihydro-2H-benzo[6,7]cyclohepta[cd]indazol-8-ylmethanol obtained in Example 1-h was treated by the procedure of Example 1-f using 500 mg of manganese dioxide, to give 210 mg of the title compound as a colorless powder.

$^1$H-NMR (400 MHz, CDCl$_3$); δ (ppm) 3.23-3.35 (4H, m), 7.00 (1H, d, J=7.7 Hz), 7.33 (1H, d, J=7.7 Hz), 7.35 (1H, d, J=7.7 Hz), 7.52 (1H, t, J=7.7 Hz), 7.82 (1H, dd, J=1.5, 7.7 Hz), 8.45 (1H, dd, J=1.5, 7.7 Hz), 10.43 (1H, s).

Example 3

6,7-Dihydro-2H-benzo[6,7]cyclohepta[cd]indazole-5-carboxaldehyde 120 mg of 6,7-dihydro-2H-benzo[6,7]cyclohepta[cd]indazol-5-ylmethanol prepared in Example 1-h was treated by the procedure of Example 1-f using 500 mg of manganese dioxide, to give 120 mg of the title compound as a colorless powder.

$^1$H-NMR (400 MHz, CDCl$_3$); δ (ppm) 3.20-3.30 (4H, m), 7.32-7.36 (2H, m), 7.36-7.41 (1H, m), 7.40 (1H, d, J=8.8 Hz), 7.89 (1H, d, J=8.8 Hz), 8.21 (1H, d, J=7.7 Hz), 10.48 (1H, s).

Example 4

6,7-Dihydro-2H-benzo[6,7]cyclohepta[cd]indazole-8-carboxylic acid 85 mg of 6,7-dihydro-2H-benzo[6,7]cyclohepta[cd]indazole-8-carboxaldehyde prepared in Example 2 was dissolved in 8 ml of dimethyl sulfoxide. To the reaction mixture was added a solution of 0.75 g of sodium dihydrogenphosphate in 4 ml water. Further, a solution of 0.25 g of sodium hypochlorite in 1 ml water was added dropwise at room temperature, followed by stirring for 0.5 hour. To the reaction mixture was added 0.01 N hydrochloric acid, and the mixture was extracted with ethyl acetate. The organic layer was washed with water, dried over anhydrous magnesium sulfate, and the solvent was evaporated. The residue was purified and separated by silica gel column chromatography (ethyl acetate:hexane=1:1), to give 85 mg of the title compound as a colorless powder.

$^1$H-NMR (400 MHz, DMSO-d$_6$); δ (ppm) 3.05-3.25 (4H, m), 6.92 (1H, d, J=7.6 Hz), 7.25 (1H, t, J=7.6 Hz), 7.36 (1H, d, J=7.6 Hz), 7.37 (1H, t, J=7.6 Hz), 7.57 (1H, dd, J=1.4, 7.6 Hz), 8.82 (1H, dd, J=1.4, 7.6 Hz), 13.05-13.25 (1H, bs), 13.28 (1H, s).

Example 5

6,7-Dihydro-2H-benzo[6,7]cyclohepta[cd]indazole-5-carboxylic acid 75 mg of 6,7-dihydro-2H-benzo[6,7]cyclohepta[cd]indazole-5-carboxaldehyde prepared in Example 3 was treated by the procedure of Example 4, and purified and separated by silica gel column chromatography (ethyl acetate:hexane=4:6), to give 47 mg of the title compound as a colorless powder.

$^1$H-NMR (400 MHz, DMSO-d$_6$); δ (ppm) 3.00-3.15 (4H, m), 7.28 (1H, dt, J=1.7, 7.3 Hz), 7.33 (1H, dd, J=1.7, 7.3 Hz), 7.33 (1H, dt, J=1.7, 7.3 Hz), 7.41 (1H, d, J=8.9 Hz), 7.78 (1H, d, J=8.9 Hz), 8.07 (1H, dd, J=1.7, 7.3 Hz), 12.65-12.70 (1H, bs), 13.43 (1H, s).

Example 6-a

6-Iodo-5-oxo-10,11-dihydro-5H-dibenzo[a,d]cyclohepten-1-ylmethanol 1.5 g of the mixture of (6-iodo-5-oxo-10,11-dihydro-5H-dibenzo[a,d]cyclohepten-1-yl)methyl acetate and (4-iodo-5-oxo-10,11-dihydro-5H-dibenzo[a,d]cyclohepten-1-yl)methyl acetate prepared in Example 1-g was dissolved in a mixed solvent of 5 ml of tetrahydrofuran and 5 ml of methanol, and 0.1 ml of 5N sodium hydroxide solution was added at room temperature, followed by stirring at room temperature for 30 minutes. Water was added to the reaction mixture, and the mixture was neutralized with 5N hydrochloric acid and extracted with ethyl acetate. The organic layer was washed with water, dried over anhydrous magnesium sulfate, and the solvent was evaporated, to give 1.3 g of a mixture of the title compound with a 4-iodo form as a colorless powder.

$^1$H-NMR (400 MHz, DMSO-d$_6$); δ (ppm) 3.03-3.07 (4H, m), 4.48 (2H, d, J=5.4 Hz), 5.21 (1H, t, J=5.4 Hz), 7.14 (1H, t, J=7.7 Hz), 7.37 (1H, dd, J=0.9, 7.7 Hz), 7.38 (1H, t, J=7.7 Hz), 7.53 (1H, dd, J=1.6, 7.7 Hz), 7.64 (1H, dd, J=1.6, 7.7 Hz), 7.74 (1H, dd, J=0.9, 7.8 Hz).

Example 6-b

6-Iodo-5-oxo-10,11-dihydro-5H-dibenzo[a,d]cycloheptene-1-carboxaldehyde 150 mg of the mixture of 6-iodo-5-oxo-10,11-dihydro-5H-dibenzo[a,d]cyclohepten-1-ylmethanol and 4-iodo form prepared in Example 6-a was oxidized by the procedure of Example 1-f using manganese dioxide, to give 120 mg of a mixture of the title compound with a 4-iodo form as a colorless powder.

$^1$H-NMR (400 MHz, DMSO-d$_6$); δ (ppm) 3.14-3.20 (2H, m), 3.65-3.71 (2H, m), 7.07 (1H, t, J=7.7 Hz), 7.24 (1H, d, J=7.7 Hz), 7.58 (1H, t, J=7.7 Hz), 7.75 (1H, d, J=7.7 Hz), 7.99 (1H, dd, J=1.4, 7.7 Hz), 8.10 (1H, dd, J=1.4, 7.7 Hz), 10.23 (1H, s).

Example 6-c

Methyl 6-iodo-5-oxo-10,11-dihydro-5H-dibenzo[a,d]cycloheptene-1-carboxylate (6-c(1))

Methyl 4-iodo-5-oxo-10,11-dihydro-5H-dibenzo[a,d]cycloheptene-1-carboxylate (6-c(2))

120 mg of the mixture of 6-iodo-5-oxo-10,11-dihydro-5H-dibenzo[a,d]cycloheptene-1-carboxaldehyde and its 4-iodo form prepared in Example 6-b was oxidized by the procedure of Example 4 using sodium hypochlorite. The resulting carboxylic acids were dissolved in 10 ml of N,N-dimethylformamide, and 0.03 ml of methyl iodide and 70 mg of potassium carbonate were added, followed by stirring at room temperature for 2 hours. Water was added to the reaction mixture, and the mixture was extracted with ethyl acetate. The organic layer was washed with water, dried over anhydrous magnesium sulfate, and the solvent was evaporated. The residue was purified and separated by silica gel column chromatography (ethyl acetate:hexane=1:10), to give 110 mg of a mixture of the title compounds as a colorless oil.

Methyl 6-iodo-5-oxo-10,11-dihydro-5H-dibenzo[a,d]cycloheptene-1-carboxylate (Major Product) (6-c(1))

$^1$H-NMR (400 MHz, CDCl$_3$); δ (ppm) 3.08-3.14 (2H, m), 3.48-3.54 (2H, m), 3.88 (3H, s), 7.04 (1H, t, J=7.8 Hz), 7.20 (1H, d, J=7.8 Hz), 7.42 (1H, t, J=7.8 Hz), 7.74 (1H, d, J=7.8 Hz), 7.97 (1H, d, J=7.8Hz), 8.00 (1H, d, J=7.8Hz).

Methyl 4-iodo-5-oxo-10,11-dihydro-5H-dibenzo[a,d]cycloheptene-1-carboxylate (6-c(2))

$^1$H-NMR (400 MHz, CDCl$_3$); δ (ppm) 3.17 3.23 (2H, m), 3.48-3.54 (2H, m), 3.93 (3H, s), 7.20 (1H, d, J=7.8 H ), 7.33

(1H, t, J=7.8 Hz), 7.45 (1H, t, J=7.8 Hz), 7.54 (1H, d, J=7.8 Hz), 7.79 (1H, d, J=7.8 Hz), 7.81 (1H, d, J=7.8 Hz).

Example 6-d

Methyl 6-iodo-5-oxo-5H-dibenzo[a,d]cycloheptene-1-carboxylate

To a solution of 260 mg of the mixture of methyl 6-iodo-5-oxo-10,11-dihydro-5H-dibenzo[a,d]cycloheptene-1-carboxylate and its 4-iodo form prepared in Example 6-c in 10 ml carbon tetrachloride were added 130 mg of N-bromosuccinimide and 5 mg of azobisisobutyronitrile, followed by heating under reflux for 2 hours. The reaction mixture was cooled to room temperature and filtered. The filtrate was washed with diethyl ether, and the solvent was removed. To the residue was added 10 ml of dimethylformamide, and further added 0.15 ml of 1,8-diazabicyclo[5.4.0]undecene at room temperature, followed by stirring at room temperature for 10 minutes. Water was added to the reaction mixture, and the mixture was extracted with ethyl acetate. The organic layer was washed with water, dried over anhydrous magnesium sulfate, and the solvent was evaporated. The residue was purified and separated by silica gel column chromatography (ethyl acetate:hexane=1:4), to give 200 mg of a mixture of the title compound with its 4-iodo form as a colorless powder.

$^1$H-NMR (400 MHz, CDCl$_3$); δ (ppm) 3.97 (3H, s), 7.09 (1H, d, J=12.6 Hz), 7.19 (1H, t, J=7.8 Hz), 7.49 (1H, d, J=7.8 Hz), 7.59 (1H, t, J=7.8 Hz), 7.76 (1H, d, J=12.6 Hz), 7.97 (1H, d, J=7.8 Hz), 8.00 (1H, d, J=7.8 Hz), 8.10 (1H, d, J=7.8 Hz).

Example 6-e 1-(Hydroxymethyl)-6-iodo-5H-dibenzo[a,d]cyclohepten-5-ol 50 mg of the mixture of methyl 6-iodo-5-oxo-5H-dibenzo[a,d]cycloheptene-1-carboxylate and its 4-iodo form prepared in Example 6-d was dissolved in 5 ml of dry tetrahydrofuran, and 0.75 ml of a 1M solution of diisobutyl aluminium hydride in toluene was added at room temperature. To the reaction mixture was added with small amounts of water and ethyl acetate, followed by stirring at room temperature for 30 minutes. Then, the reaction mixture was filtered through Celite, washed with ethyl acetate, and the solvent was removed, to give 40 mg of a mixture of the title compound with its 4-iodo form as a colorless powder.

$^1$H-NMR (400 MHz, CDCl$_3$); δ (ppm) 4.85 (1H, d, J=12.5 Hz), 4.91 (1H, d, J=12.5 Hz), 6.40 (1H, d, J=8.3 Hz), 6.99 (1H, t, J=7.6 Hz), 7.19 (1H, d, J=12.0 Hz), 7.42 (1H, t, J=7.6 Hz), 7.43 (1H, d, J=7.6 Hz), 7.44 (1H, d, J=7.6 Hz), 7.50 (1H, d, J=12.0 Hz), 7.66 (1H, d, J=7.6 Hz), 7.90 (1H, d, J=7.6 Hz).

Example 6-f (5-Hydroxy-6-iodo-5H-dibenzo[a,d]cyclohepten-1-yl)methyl acetate 310 mg of the mixture of 1-(hydroxymethyl)-6-iodo-5H-dibenzo[a,d]cyclohepten-5-ol with its 4-iodo form prepared in Example 6-e was dissolved in 15 ml of methylene chloride, and 100 mg of 4-(dimethylamino)pyridine and 0.8 ml of 1M solution of acetic anhydride in tetrahydrofuran were added under ice-cooling, followed by stirring at room temperature for 2 hours. The solvent was evaporated, and the residue was purified and separated by silica gel column chromatography (ethyl acetate:hexane=3:17), to give 230 mg of a mixture of the title compound with its 4-iodo form as a colorless powder.

$^1$H-NMR (400 MHz, CDCl$_3$); δ (ppm) 2.12 (3H, s), 2.70-2.90 (1H, bs), 5.28 (2H, s), 6.40 (1H, s), 6.99 (1H, t, J=7.8 Hz), 7.19 (1H, d, J=12.3 Hz), 7.37 (H, d, J=12.3 Hz), 7.40-7.45 (3H, m), 7.66-7.71 (1H, m), 7.90 (1H, dd, J=1.4, 7.8 Hz).

Example 6-g

[5-(Acetyloxy)-6-iodo-5H-dibenzo[a,d]cyclohepten-1-yl]methyl acetate 80 mg of a mixture of the title compound with its 4-iodo form was obtained as a colorless oil as a by-product in Example 6-f.

$^1$H-NMR (400 MHz, CDC13); δ (ppm) 1.84 (3H, s), 2.12 (3H, s), 5.29 (2H, s), 7.00 (1H, t, J=7.8 Hz), 7.10 (1H, d, J=12.2 Hz), 7.24 (1H, d, J=12.2 Hz), 7.38-7.46 (3H, m), 7.40 (1H, s), 7.76-7.81 (1H, m), 7.90 (1H, dd, J=1.3, 7.8 Hz).

Example 6-h (6-Iodo-5-oxo-5H-dibenzo[a,d]cyclohepten-1-yl)methyl acetate 230 mg of the mixture of (5-hydroxy-6-iodo-5H-dibenzo[a,d]cyclohepten-1-yl)methyl acetate with its 4-iodo form prepared in Example 6-f was oxidized by the procedure of Example 1-f, to give 200 mg of a mixture of the title compound with its 4-iodo form as a colorless powder.

$^1$H-NMR (400 MHz, CDCl$_3$); δ (ppm) 2.10 (3H, s), 5.33 (2H, s), 7.07 (1H, d, J=12.6 Hz), 7.18 (1H, t, J=7.6 Hz), 7.24 (1H, d, J=12.6 Hz), 7.48 (1H, d, J=7.6 Hz), 7.55 (1H, t, J=7.6 Hz), 7.62 (1H, dd, J=1.4, 7.6 Hz), 7.83 (1H, dd, J=1.4, 7.6 Hz), 8.02 (1H, d, J=7.6 Hz).

Example 6-i

2H-Benzo[6,7]cyclohepta[cd]indazol-8-ylmethanol (6-i(1))

2H-Benzo[6,7]cyclohepta[cd]indazol-5-ylmethanol (6-i(2))

The mixture of (6-iodo-5-oxo-5H-dibenzo[a,d]cyclohepten-1-yl)methyl acetate with its 4-iodo form prepared in Example 6-h was treated with hydrazine monohydrate by the procedure of Example 1-h, and purified and separated by silica gel column chromatography (ethyl acetate:hexane=3:7), to give 320 mg and 1.1 mg of the title compounds as yellow powders, respectively.

2H-Benzo[6,7]cyclohepta[cd]indazol-8-ylmethanol (Major Product) (6-i(1))

$^1$H-NMR (400 MHz, DMSO-d$_6$); δ (ppm) 4.56 (2H, d, J=5.5 Hz), 5.25 (1H, t, J=5.5 Hz), 6.41 (1H, d, J=12.7 Hz), 6.57 (1H, d, J=12.7 Hz), 6.61-6.66 (1H, m), 7.05-7.11 (2H, m), 7.20 (1H, t, J=7.8 Hz), 7.26 (1H, d, J=7.8 Hz), 8.05 (1H, d, J=7.8 Hz), 12.89 (1H, bs).

2H-Benzo[6,7]cyclohepta[cd]indazol-5-ylmethanol (6-i(2))

$^1$H-NMR (400 MHz, DMSO-d$_6$); δ (ppm) 4.47 (2H, d, J=5.5 Hz), 5.01 (1H, t, J=5.5 Hz), 6.34 (1H, d, J=12.8 Hz), 6.63 (1H, d, J=12.8 Hz), 7.07 (1H, d, J=8.8 Hz), 7.15 (1H, d, J=8.8 Hz), 7.17-7.21 (2H, m), 7.21-7.27 (1H, m), 8.14 (1H, d, J=8.3 Hz), 12.86 (1H, bs).

Example 7

2H-Benzo[6,7]cyclohepta[cd]indazole-8-carboxylic 18 mg of 2H-benzo[6,7]cyclohepta[cd]indazol-8-yl-methanol prepared in Example 6-i was oxidized by the procedure of Example 1-f using manganese dioxide, and further oxidized by the procedure of Example 4 using sodium hypochlorite, to give 8 mg of the title compound as a yellow powder.

$^1$H-NMR (400 MHz, CD$_3$OD); δ (ppm) 6.42 (1H, d, J=12.8 Hz), 6.62-6.68 (1H, m), 6.66 (1H, d, J=12.8 Hz), 7.04-7.16 (2H, m), 7.26 (1H, t, J=7.6 Hz), 7.38 (1H, dd, J=1.7, 7.6 Hz), 8.33 (1H, dd, J=1.7, 7.6 Hz).

Example 8-a

Benzyl N-(6-iodo-5-oxo-10,11-dihydro-5H-dibenzo [a,d]cyclohepten-1-yl)carbamate

To a solution of 200 mg of 6-iodo-5-oxo-10,11-dihydro-5H-dibenzo[a,d]cycloheptene-1-carboxylic acid obtained as an intermediate in Example 6-c in 10 ml dry tetrahydrofuran were added 0.08 ml of triethylamine and 0.13 ml of diphenylphosphoryl azide at room temperature, followed by stirring for 30 minutes. To the reaction mixture was added 1 ml of benzyl alcohol and the mixture was heated under reflux for 6 hours. Water was added to the reaction mixture and the mixture was and extracted with ethyl acetate. The organic layer was washed with water, dried over anhydrous magnesium sulfate, and the solvent was evaporated. The residue was purified and separated by silica gel column chromatography (ethyl acetate:hexane=1:3), to give 200 mg of the title compound as a colorless powder.

$^1$H-NMR (400 MHz, DMSO-d$_6$); δ (ppm) 2.99-3.04 (4H, m), 5.11 (2H, s), 7.15 (1H, t, J=7.8 Hz), 7.27-7.32 (2H, m), 7.34-7.40 (3H, m), 7.36 (1H, dd, J=1.0, 7.8 Hz), 7.40 (1H, t, J=7.8 Hz), 7.51 (1H, dd, J=1.6, 7.8 Hz), 7.56 (1H, bd, J=7.8 Hz), 7.76 (1H, dd, J=1.0, 7.8 Hz), 9.06 (1H, bs).

Example 8-b 6,7-Dihydro-2H-benzo[6,7]cyclohepta[cd]indazole-8-amine 50 mg of benzyl N-(6-iodo-5-oxo-10,11-dihydro-5H-dibenzo[a,d]cyclohepten-1-yl)carbamate prepared in Example 8-a was treated with hydrazine monohydrate by the procedure of Example 1-h and purified and separated by silica gel column chromatography (ethyl acetate:hexane=1:2), to give 15 mg of the title compound as a colorless powder.

$^1$H-NMR (400 MHz, CDCl$_3$); δ (ppm) 3.05-3.15 (2H, m), 3.15-3.25 (2H, m), 3.50-3.80 (2H, bs), 6.78 (1H, d, J=7.8 Hz), 6.93 (1H, bd, J=7.8 Hz), 7.16 (1H, t, J=7.8Hz), 7.28 (1H, d, J=7.8Hz), 7.28 (1H, t, J=7.8Hz), 7.72 (1H, d, J=7.8Hz).

Example 9-a

4-Iodo-5H-dibenzo[a, d]cyclohepten-5-one 2.06 g of dibenzosuberenone [CAS No. 2222-33-5] was subjected to the procedure of Example 1-g using 6.5 g of thallium trifluoroacetate and 2.0 g of potassium iodide, to give 1.0 g of a mixture of the title compound with dibenzosuberenone as a colorless powder.

$^1$H-NMR (400 MHz, CDCl$_3$); δ (ppm) 6.97 (1H, d, J=12.3 Hz), 7.07 (1H, d, J=12.3 Hz), 7.18 (1H, t, J=7.8 Hz), 7.48 (1H, d, J=7.8 Hz), 7.49 (1H, dd, J=1.9, 7.0 Hz), 7.56 (1H, dt, J=1.9, 7.0 Hz), 7.59 (1H, dt, J=1.9, 7.0 Hz), 7.90 (1H, dd, J=1.9, 7.0 Hz), 8.04 (1H, d, J=7.8 Hz).

Example 9-b

2H-Benzo[6,7]cyclohepta[cd]indazole

The mixture of 4-iodo-5H-dibenzo[a,d]cyclopenten-5-one with dibenzosuberene prepared in Example 9-a was treated by the procedure of Example 1-h, and purified and separated by silica gel column chromatography (ethyl acetate:hexane=1:3), to give 45 mg of the title compound as a yellow powder.

$^1$H-NMR (400 MHz, CDCl$_3$); δ (ppm) 6.29 (1H, d, J=12.6 Hz), 6.38 (1H, d, J=12.6 Hz), 6.68 (1H, d, J=7.5 Hz), 7.07 (1H, d, J=7.5 Hz), 7.12 (1H, d, J=7.5 Hz), 7.15 (1H, t, J=7.5 Hz), 7.21 (1H, t, J=7.5 Hz), 7.26 (1H, t, J=7.5 Hz), 8.29 (1H, d, J=7.5 Hz).

The compounds of Examples 10 to 21 were synthesized according to the following Synthesis Process A.

Synthesis Process A

Each 30 mg of the indazolecarboxylic acids synthesized in Examples 4, 5 and 7 in 1.5 ml of N,N-dimethylformamide solution were pipetted into several test tubes in 0.3 ml portions. To the each solution was added 1.1 equivalent of an amine. To the each reaction mixture were sequentially added 30 µl of 1 M solution of 1-hydroxybenzotriazole in N,N-dimethylformamide, 10 mg of 1-ethyl-3-(3-dimethylaminopropyl)carbodiimide hydrochloride (=WSC.HCl), and 20 µl of diisopropylethylamine. The mixture was subjected to sonication for 10 minutes and left stand for one day. Each of the reaction mixtures was purified and separated by LC-MS (developing solvent (eluent); acetonitrile:water=0:100 to 100:0/20 minute-cycle, flow rate: 20 ml/min, column: YMC Combiprep ODS-AM), to give the test compounds.

Example 10

N8-Cyclopropyl-6,7-dihydro-2H-benzo[6,7]cyclohepta[cd]indazole-8-carboxamide

MS (ESI)m/z 304 MH$^+$

Example 11

N8-(2-Furylmethyl)-6,7-dihydro-2H-benzo[6,7]cyclohepta[cd]indazole-8-carboxamide MS (ESI)m/z 344 MH$^+$

Example 12

N8-[2-(Acetylamino)ethyl]-6,7-dihydro-2H-benzo[6,7]cyclohepta[cd]indazole-8-carboxamide MS (ESI)m/z 349 MH$^+$

Example 13

N8-[1-(Hydroxymethyl)-2-methylpropyl]-6,7-dihydro-2H-benzo[6,7]cyclohepta[cd]indazole-8-carboxamide MS (ESI)m/z 350 MH$^+$

Example 14

N8-(3-Pyridylmethyl)-6,7-dihydro-2H-benzo[6,7]cyclohepta[cd]indazole-8-carboxamide MS (ESI)m/z 355 MH$^+$

Example 15

N5-Cyclopropyl-6,7-dihydro-2H-benzo[6,7]cyclohepta[cd]indazole-5-carboxamide

MS (ESI)m/z 304 MH$^+$

Example 16

N5-(2-Furylmethyl)-6,7-dihydro-2H-benzo[6,7]cyclohepta[cd]indazole-5-carboxamide MS (ESI)m/z 344 MH$^+$

Example 17

N5-[2-(Acetylamino)ethyl]-6,7-dihydro-2H-benzo[6,7]cyclohepta[cd]indazole-5-carboxamide MS (ESI)m/z 349 MH$^+$

Example 18

N5-[1-(Hydroxymethyl)-2-methylpropyl]-6,7-dihydro-2H-benzo[6,7]cyclohepta[cd]indazole-5-carboxamide MS (ESI)m/z 350 MH$^+$

Example 19

N5-(3-Pyridylmethyl)-6,7-dihydro-2H-benzo[6,7]cyclohepta[cd]indazole-5-carboxamide MS (ESI)m/z 355 MH$^+$

Example 20

N8-(2-Furylmethyl)-2H-benzo[6,7]cyclohepta[cd]indazole-8-carboxamide

MS (ESI)m/z 342 MH$^+$

Example 21

N8-Cyclopropyl-2H-benzo[6,7]cyclohepta[cd]indazole-8-carboxamide $^1$H-NMR (400 MHz, CD$_3$OD); δ (ppm) 0.62 (2H, dt, J=2.0, 5.1 Hz), 0.82 (2H, dt, J=5.1, 7.1 Hz), 2.84-2.93 (1H, m), 6.33 (1H, d, J=12.6 Hz), 6.42 (1H, d, J=12.6 Hz), 6.66 (1H, dd, J=2.6, 5.6 Hz), 7.09-7.16 (3H, m), 7.25 (1H, t, J=7.6 Hz), 8.29 (1H, d, J=7.6 Hz).

MS (ESI)m/z 302 MH$^+$

Example 22

N1-(6,7-Dihydro-2H-benzo[6,7]cyclohepta[cd]indazol-8-yl)-1-cyclopropanecarboxamide 6,7-Dihydro-2H-benzo[6,7]cyclohepta[cd]indazole-8-amine prepared in Example 8 and cyclopropanecarboxylic acid were subjected to the reaction and purified and separated by LC-MS in the same manner as in Synthesis Process A, to give the title compound.

MS (ESI)m/z 302 MH$^+$

Example 23

6,7-Dihydro-2H-benzo[6,7]azepino[5,4,3-cd]indazol-6-one (23(1))

6,7-Dihydro-2H-benzo[5,6]azepino[4,3,2-cd]indazol-7-one (23(2))

To a solution of 100 mg of 2,6-dihydrodibenzo[cd,g]indazol-6-one [CAS No. 129-56-6] in 0.6 ml concentrated sulfuric acid was added 78 mg of sodium azide [CAS No. 26628-22-8], followed by stirring at room temperature for 3 days. After adding ice, the reaction mixture was poured into a mixture solution of 100 ml of ethyl acetate and 10 ml of tetrahydrofuran and washed with saturated sodium hydrogen carbonate solution. The organic layer was washed with brine, dried over anhydrous magnesium sulfate, and the solvent was evaporated. The residue was dissolved in tetrahydrofuran, adsorbed by 3.5 g of silica gel and subjected to silica gel chromatography [Wako Gel C-200, 2 g]. The fractions of tetrahydrofuran-toluene [19:1 to 9:1] were concentrated, and the resulting powder was suspended in tetrahydrofuran-toluene. A powder was collected by filtration, and recrystallized from dimethylformamide-water, to give 27 mg of 6,7-dihydro-2H-benzo[6,7]azepino[5,4,3-cd]indazol-6-one as green needles.

$^1$H-NMR (400 MHz, DMSO-d$_6$); δ (ppm) 7.12 (1H, t, J=7.6 Hz), 7.28 (1H, td, J=1.6, 7.6 Hz), 7.38 (1H, d, J=7.6 Hz), 7.51 (1H, t, J=7.6 Hz), 7.75 (1H, d, J=7.6 Hz), 7.84 (1H, d, J=7.6 Hz), 8.31 (1H, dd, J=1.6, 7.6 Hz), 10.28 (1H, s), 13.51 (1H, s)

The mother liquor of tetrahydrofuran-toluene suspension was concentrated, subjected to preparative thin layer chromatography [Merck, Kieselgel 60, 20 cm×20 cm, thickness: 5 mm], developed by ethyl acetate-hexane 1:3 and then 1:1, the target band was extracted with tetrahydrofuran, and the solvent was evaporated, to give 0.3 mg of 6,7-dihydro-2H-benzo[5,6]azepino[4,3,2-cd]indazol-7-one as bright yellow crystals.

$^1$H-NMR (400 MHz, DMSO-d$_6$); δ (ppm) 6.63 (1H, d, J=7.6 Hz), 6.99 (1H, t, J=7.6 Hz), 7.19 (1H, d, J=7.6 Hz), 7.40 (1H, t, J=7.6 Hz), 7.61 (1H, t, J=7.6 Hz), 8.37 (1H, d, J=7.6 Hz), 8.39 (1H, d, J=7.6 Hz), 10.63 (1H, s), 13.23 (1H, s)

Example 24

5-Chloro-6,7-dihydro-2H-benzo[5,6]azepino[4,3,2-cd]indazol-7-one

To a solution of 1.02 g of 5-chloro-2,6-dihydrodibenzo[cd,g]indazol-6-one [synthesized from 1,4-dichloroanthraquinone [CAS No. 602-25-5] as a starting material according to the method described in Patent No. WO-0112609] in 5 ml concentrated sulfuric acid was added 0.78 g of sodium azide [CAS No. 26628-22-8], followed by stirring at room temperature for 2 days. The reaction mixture was poured onto 50 ml of ice-water, the precipitated powder was collected by filtration and dried in vacuo. The powder was dissolved in 10 ml of dimethylformamide and 5 ml of ethyl acetate was added. To the suspension was added saturated aqueous sodium hydrogencarbonate solution, and stirred. The crystals were collected by filtration, sequentially washed with hydrous dimethylformamide and water and dried in vacuo, to give 647 mg of the title compound as green crystals.

$^1$H-NMR (400 MHz, DMSO-d$_6$); δ (ppm) 7.11 (1H, d, J=8.8 Hz), 7.33 (1H, d, J=8.8 Hz), 7.45 (1H, dt, J=1.2, 8.0 Hz), 7.67 (1H, dt, J=1.2, 8.0 Hz), 8.38 (1H, dd, J=1.2, 8.0 Hz), 8.41 (1H, dd, J=1.2, 8.0 Hz), 8.64 (1H, s), 13.60 (1H, br s)

Example 25-a

1-Chloro-4-methyl-9,10-dihydro-9,10-anthracenedione

To 30 g of phthalic anhydride [CAS No. 85-44-9] and 50 ml of 4-chlorotoluene [CAS No. 103-63-9] was added 60 g of aluminium trichloride [CAS No. 7446-70-0], and the mixture was stirred at 80° C. for 5 hours and then left stand to cool. To the reaction mixture was added 150 ml of methylene chloride and the mixture was added dropwise to 500 ml of ice-water. 30 ml of concentrated hydrochloric acid was added, and then the mixture was extracted with ethyl acetate. The organic layer was sequentially washed with water and brine, dried over anhydrous magnesium sulfate, and the solvent was removed. To the resulting residue were added diethyl ether and water, and then sodium carbonate was added to basify. The aqueous layer was washed with diethyl ether, to remove excess 4-chlorotoluene. The aqueous layer was acidified with concentrated hydrochloric acid, and then it was extracted with ethyl acetate. The ethyl acetate layer was washed with brine, dried over anhydrous magnesium sulfate, and the solvent was removed.

The resulting residue was dissolved in 45 ml of concentrated sulfuric acid and stirred at 115° C. for 6 hours. The reaction mixture was added dropwise to 500 ml of ice-water and extracted with ethyl acetate. The organic layer was sequentially washed with saturated aqueous sodium hydrogencarbonate solution and brine, dried over anhydrous magnesium sulfate, filtered through an alumina pad and treated with activated carbon. After removing the activated carbon by filtration, the solvent was removed, to give 32.3 g of the title compound as light brown crystals.

$^1$H-NMR (400 MHz, DMSO-d$_6$); δ (ppm) 2.74 (3H, s), 7.68 (1H, d, J=8.0 Hz), 7.82 (1H, d, J=8.0 Hz), 7.89 (2H, td, J=7.2, 4.0 Hz), 8.10 (1H, dd, J=4.0, 7.2 Hz), 8.11 (1H, dd, J=4.0, 7.2 Hz)

Example 25-b

5-Methyl-2,6-dihydrodibenzo[cd,g]indazol-6-one

To a solution of 32.3 g of 1-chloro-4-methyl-9,10-dihydro-9,10-anthracenedione prepared in Example 25-a in 150 ml pyridine was added 15 ml of hydrazine monohydrate [CAS No. 7803-57-8], followed by stirring at 90° C. overnight. After removing the solvent, to the resulting residue was added 65 ml of ethanol to give crystals. The crystals were collected by filtration, sequentially washed with moisture ethanol and ethanol, and dried in vacuo, to give 26.6 g of the title compound as ocher yellow needles.

$^1$H-NMR (400 MHz, DMSO-d$_6$); δ (ppm) 2.87 (3H, s), 7.55 (1H, d, J=8.4 Hz), 7.61 (1H, t, J=8.0 Hz), 7.81 (1H, t, J=8.0 Hz), 7.90 (1H, d, J=8.4 Hz), 8.21 (1H, d, J=8.0 Hz), 8.32 (1H, d, J=8.0 Hz), 13.71 (1H, br s)

Example 25-c

5-Methyl-6,7-dihydro-2H-benzo[5,6]azepino[4,3,2-cd]indazol-7-one

To a solution of 15 g of 5-methyl-2,6-dihydrodibenzo[cd,g]indazol-6-one prepared in Example 25-b in 70 ml concentrated sulfuric acid was added 12.5 g of sodium azide [CAS No. 26628-22-8], followed by stirring at room temperature for 30 hours. The reaction mixture was poured onto 700 ml of ice-water, the precipitated powder was collected by filtration and dried in vacuo. The resulting powder was dissolved in a solvent mixture of dimethylformamide-ethyl acetate, sequentially washed with saturated aqueous sodium hydrogencarbonate solution and brine, dried over anhydrous magnesium sulfate, and the solvent was evaporated. The residue was recrystallized from dimethylformamide-ethyl acetate, to give 6.59 g of the title compound as ocher yellow crystals.

$^1$H-NMR (400 MHz, DMSO-d$_6$); δ (ppm) 2.50 (3H, s), 6.97 (1H, d, J=8.4 Hz), 7.11 (1H, d, J=8.4 Hz), 7.40 (1H, t, J=8.0 Hz), 7.61 (1H, t, J=8.0 Hz), 8.35 (2H, d, J=8.0 Hz), 8.88 (1H, s), 13.17 (1H, s)

Example 26

3-Bromo-5-methyl-6,7-dihydro-2H-benzo[5,6]azepino[4,3,2-cd]indazol-7-one

To a solution of 50 mg of 5-methyl-6,7-dihydro-2H-benzo[5,6]azepino[4,3,2-cd]indazol-7-one prepared in Example 25-c in 1 ml dimethylformamide was added 40 mg of N-bromosuccinimide [CAS No. 128-08-5], followed by stirring at room temperature for 30 minutes. To the reaction mixture was added 2 ml of ethyl acetate and the precipitated crystals were collected by filtration. The crystals were washed with ethyl acetate and dried in vacuo, to give 45 mg of the title compound as ocher yellow crystals.

$^1$H-NMR (400 MHz, DMSO-$d_6$); δ (ppm) 2.33 (3H, s), 7.39 (1H, s), 7.44 (1H, dt, J=1.6, 8.0 Hz), 7.65 (1H, dt, J=1.6, 8.0 Hz), 8.36 (1H, dd, J=1.6, 8.0 Hz), 8.38 (1H, dd, J=1.6, 8.0 Hz), 9.01 (1H, s), 13.59 (1H, s)

The compounds (I) according to the present invention or a salt thereof exhibited an excellent action in tests for determining JNK inhibitory action. For example, the inhibitory actions on JNK 3 were as follows.

Test Example 1 Determination of JNK 3 Inhibition

Human JNK 3 was expressed as a fusion protein (GST-JNK 3) with glutathione S-transferase (GST) in *Escherichia coli* and was purified using glutathione Sepharose 4B beads. The amino acid sequence 1-169 of c-Jun was peppered as a fusion protein (GST-c-Jun) with GST in *Escherichia coli*, was purified using glutathione Sepharose 4B beads and was used as a substrate. A test compound was diluted with 100% dimethyl sulfoxide into 10 mM and was then further diluted with 10% aqueous dimethyl sulfoxide solution to yield a dilution series. To each well of 96-well OPTI plate (available from Packard) were placed 20 μl of the diluted compound, 30 μl of a substrate solution (1.2 μg of GST-c-Jun, 0.04 μg of GST-JNK 3, 0.2 μCi of [γ-$^{33}$P]ATP, 25 mM of HEPES pH=7.5, 10 mM of magnesium acetate, and 3.33 μM of ATP), and 50 μl of an enzyme solution (0.04 μg of GST-JNK 3, 25 mM of HEPES pH=7.5, and 10 mM magnesium acetate) up to 100 μl, and the mixture was allowed to react for 30 minutes. After terminating the reaction by adding 100 μl of a reaction terminator (80 mM ATP, 5 mg/ml glutathione SPA beads (available from Amersham Pharmacia Biotech)), the reaction mixture was shaken for 30 minutes. The mixture was centrifuged at room temperature at 1000×g for 5 minutes, and the emission intensity thereof was determined on a TopCount™ illuminator (available from Packard). The activity is expressed by the 50% inhibitory concentration on the enzymatic activity of JNK, i.e., $IC_{50}$ (nM).

Results: The following compounds showed $IC_{50}$ of 300 nM or less on JNK 3.

Example 1: 6,7-Dihydro-2H-benzo[6,7]cyclohepta[cd]indazol-8-ylmethanol
Example 6: 2H-Benzo[6,7]cyclohepta[cd]indazol-8-ylmethanol
Example 8: 6,7-Dihydro-2H-benzo[6,7]cyclohepta[cd]indazole-8-amine
Example 9: 2H-Benzo[6,7]cyclohepta[cd]indazole
Example 20: N8-(2-Furylmethyl)-2H-benzo[6,7]cyclohepta[cd]indazole-8-carboxamide
Example 21: N8-Cyclopropyl-2H-benzo[6,7]cyclohepta[cd]indazole-8-carboxamide
Example 23: 6,7-Dihydro-2H-benzo[6,7]azepino[5,4,3-cd]indazol-6-one; 6,7-Dihydro-2H-benzo[5,6]azepino[4,3,2-cd]indazol-7-one
Example 25: 5-Methyl-6,7-dihydro-2H-benzo[5,6]azepino[4,3,2-cd]indazol-7-one
Example 26: 3-Bromo-5-methyl-6,7-dihydro-2H-benzo[5,6]azepino[4,3,2-cd]indazol-7-one The structural formulae of the compounds according to the above-mentioned Examples will be shown below.

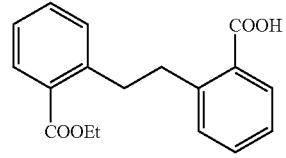

Example 1-a

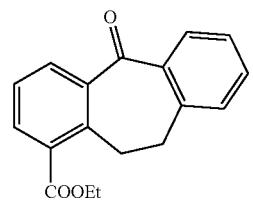

Example 1-b

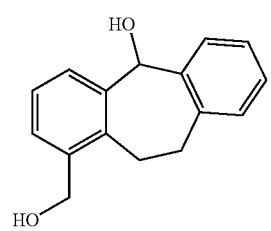

Example 1-c

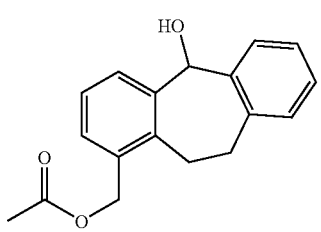

Example 1-d

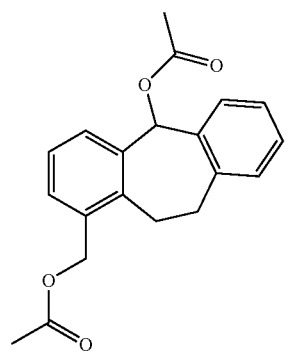

Example 1-e

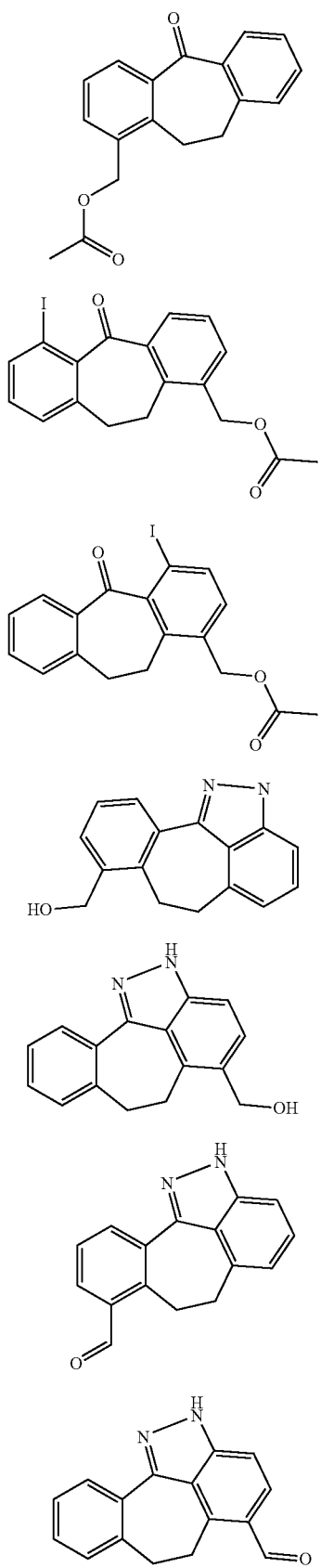
Example 1-f
Example 1-g (1)
Example 1-g (2)
Example 1-h (1)
Example 1-h (2)
Example 2
Example 3
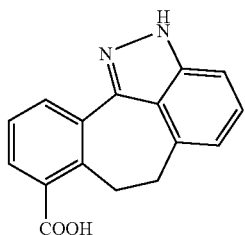
Example 4
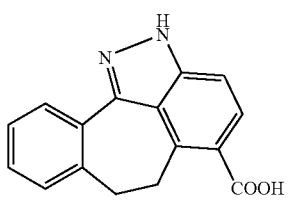
Example 5
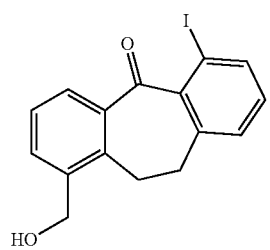
Example 6-a
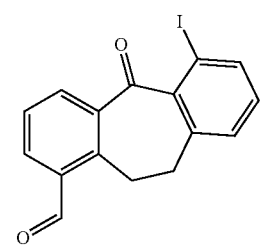
Example 6-b
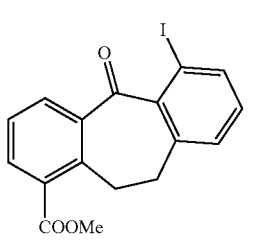
Example 6-c (1)
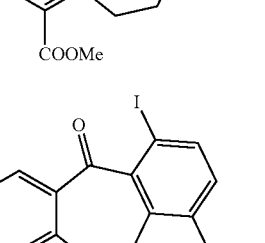
Example 6-c (2)
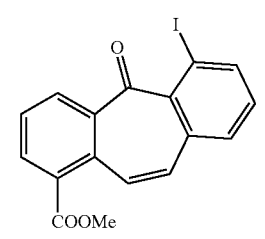
Example 6-d -continued
Example 6-e
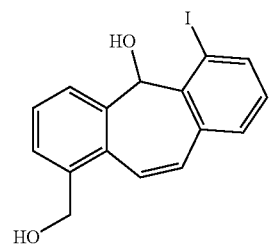
Example 6-f
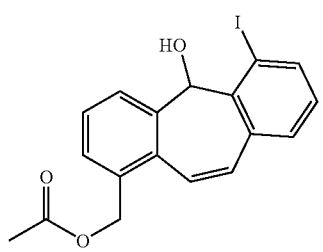
Example 6-g
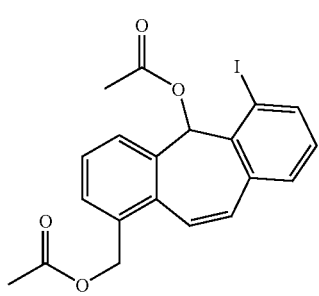
Example 6-h
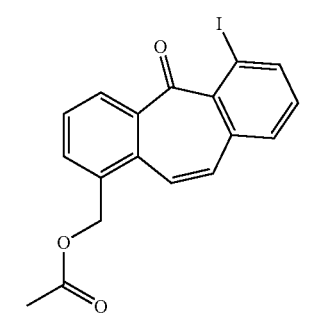
Example 6-i (1)
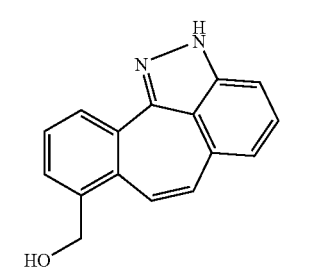
Example 6-i (2)
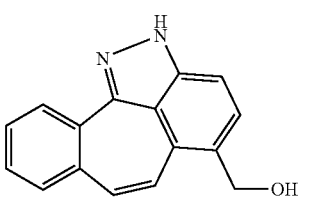
-continued
Example 7
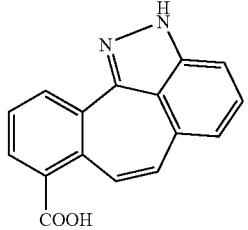
Example 8-a
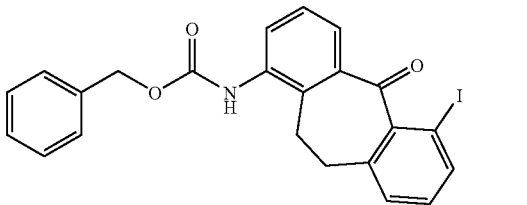
Example 8-b
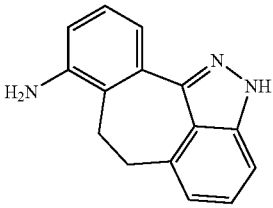
Example 9-a
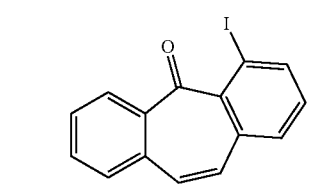
Example 9-b
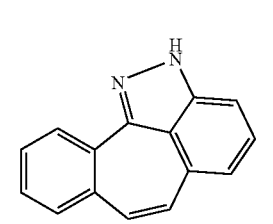
Example 10
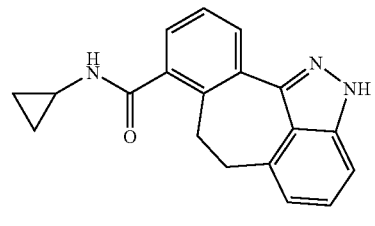
Example 11
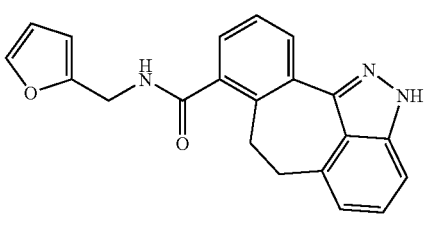

Example 12
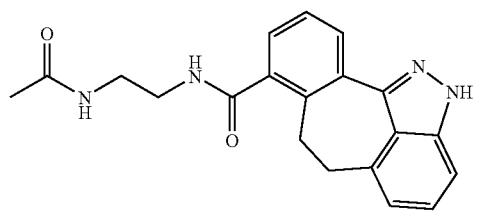
Example 13
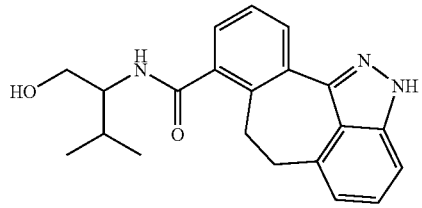
Example 14
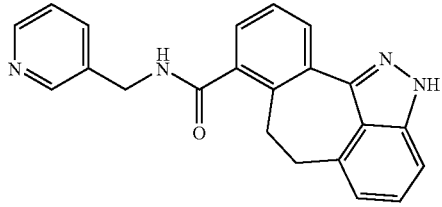
Example 15
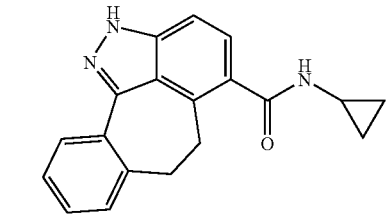
Example 16
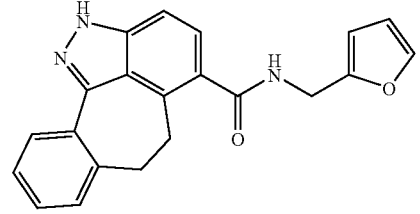
Example 17
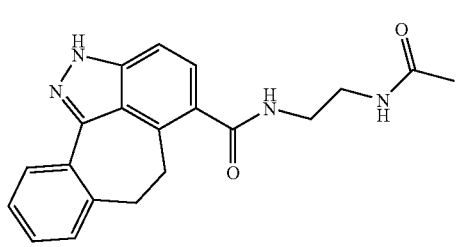
Example 18
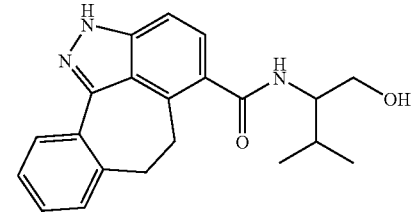
Example 19
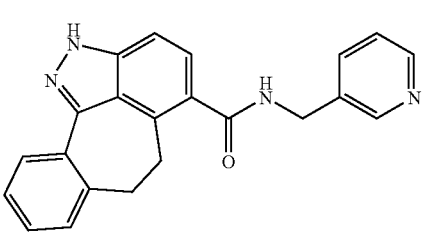
Example 20
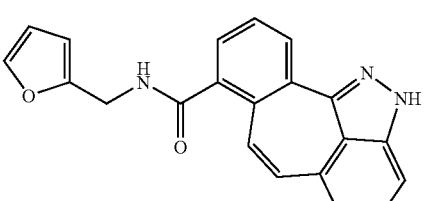
Example 21
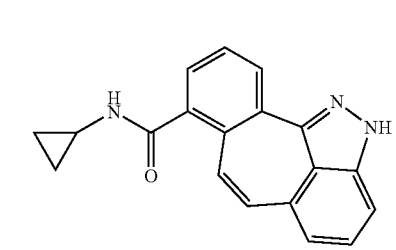
Example 22
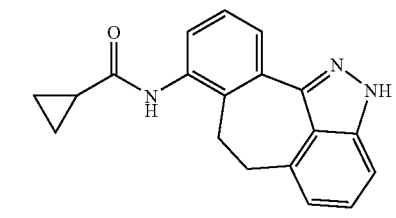
Example 23 (1)
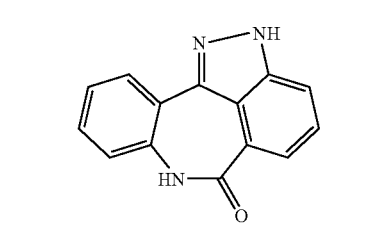
Example 23 (2)
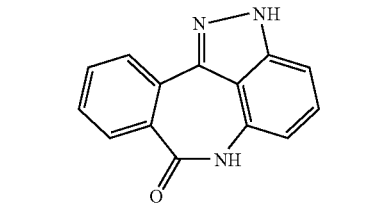
Example 24
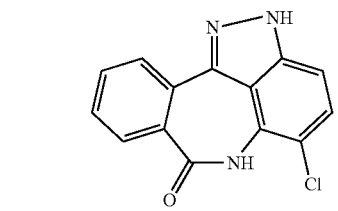

Example 25-a
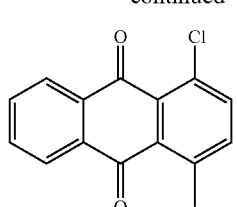

Example 25-b
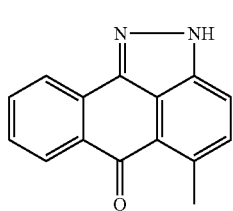

Example 25-c
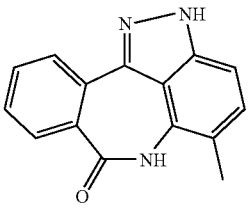

Example 26
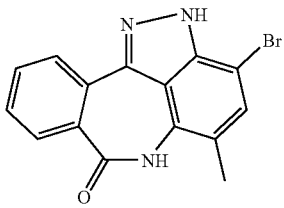

The invention claimed is:

1. A compound represented by the following formula, a salt thereof or a hydrate of them

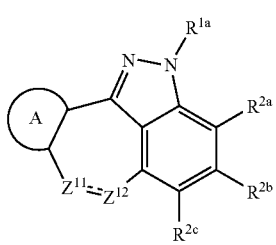
(I)

wherein $Z^{11}$ and $Z^{12}$ each independently represent a carbonyl group, an oxygen atom, a sulfur atom, or a methine group which may be substituted, a methylene group which may be substituted or a nitrogen atom which may be substituted; - - - - - represents a double bond or a single bond; $R^{1a}$ represents a hydrogen atom, a $C_1$-$C_6$ alkyl group, a phenyl group or a benzyl group; $R^{2a}$, $R^{2b}$ and $R^{2c}$ each independently represent a group selected from Substituent Group (a); the ring A represents a benzene ring which may have one to three groups selected from Substituent Group (a), a naphthalene ring which may have one to three groups selected from Substituent Group (a) or a 5- to 10-membered aromatic heterocyclic ring which may have one to three groups selected from Substituent Group (a);

Substituent Group (a)
(1) a hydrogen atom, (2) halogen atoms, (3) a nitro group, (4) a hydroxyl group, (5) a cyano group, (6) a carboxyl group, (7) an amino group, (8) a formyl group or (9) a group represented by the formula:

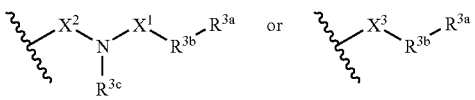

wherein $X^1$ and $X^2$ each independently represent a single bond, —CO—, —SO$_2$— or $C_1$-$C_6$-methylene group; $X^3$ represents a single bond, —CO—, —SO$_2$, —O—, —CO—O— or —O—CO—; $R^{3b}$ represents a $C_1$-$C_6$ alkylene group or a single bond; $R^{3a}$ and $R^{3c}$ represent a hydrogen atom, a $C_1$-$C_6$ alkyl group which may be substituted, a $C_2$-$C_6$ alkenyl group which may be substituted, a $C_2$-$C_6$ alkynyl group which may be substituted, a $C_3$-$C_8$ cycloalkyl group which may be substituted, a $C_6$-$C_{14}$ aromatic cyclic hydrocarbon group which may be substituted, a 5- to 14-membered aromatic heterocyclic group which may be substituted or a hydrogen atom, provided that 6,7-dihydrobenzo[1,2]cyclohepta[3,4,5-cd]indazole is excluded.

2. A compound represented by the following formula, a salt thereof or a hydrate of them:

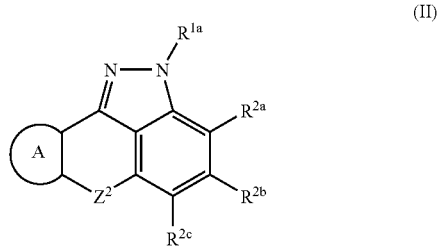
(II)

wherein $Z^2$ represents a 1,2-ethylene group which may be substituted, a 1,2-vinylene group which may be substituted, an oxymethylene group which may be substituted, an aminomethylene group which may be substituted, an amide group which may be substituted or an ester group; and the ring A, $R^{1a}$, $R^{2a}$, $R^{2b}$ and $R^{2c}$ have the same meanings as the ring A, $R^{1a}$, $R^{2a}$, $R^{2b}$ and $R^{2c}$ described in claim 1, provided that 6,7-dihydrobenzo[1,2]cyclohepta[3,4,5-cd]indazole is excluded.

3. A compound represented by the following formula, a salt thereof or a hydrate of them

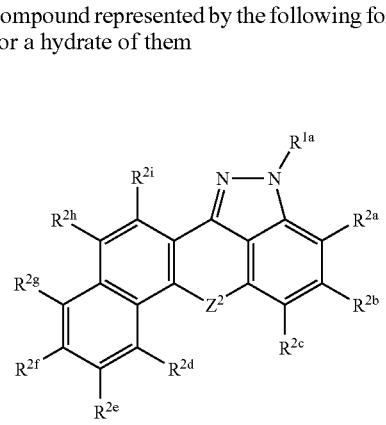
(III)

wherein $R^{1a}$, $R^{2a}$, $R^{2b}$ and $R^{2c}$ have the same meanings as $R^{1a}$, $R^{2a}$, $R^{2b}$ and $R^{2c}$ described in claim 1, respectively; $Z^2$ represents a 1,2-ethylene group which may be substituted, a 1,2-vinylene group which may be substituted, an oxymethylene group which may be substituted, an aminomethylene group which may be substituted, an amide group which may be substituted, or an ester group; and $R^{2d}$, $R^{2e}$, $R^{2f}$, $R^{2g}$, $R^{2h}$ and $R^{2i}$ each independently represent a substituent selected from the Substituent Group (a) described in claim 1.

4. A compound represented by the following formula, a salt thereof or a hydrate of them:

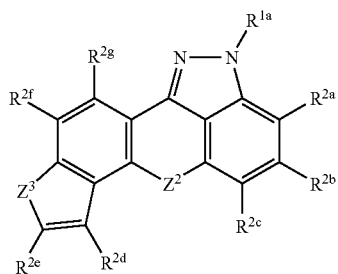

(IV)

wherein $R^{1a}$, $R^{2a}$, $R^{2b}$ and $R^{2c}$ have the same meanings as $R^{1a}$, $R^{2a}$, $R^{2b}$ and $R^{2c}$ described in claim 1, respectively; $Z^2$ represents a 1,2-ethylene group which may be substituted, a 1,2-vinylene group which may be substituted, an oxymethylene group which may be substituted, an aminomethylene group which may be substituted, an amide group which may be substituted, or an ester group; $R^{2d}$, $R^{2e}$, $R^{2f}$ and $R^{2g}$ each independently represent a substituent selected from the Substituent Group (a) described in claim 1; and $Z^3$ represents a nitrogen atom, an oxygen atom, a sulfur atom or a group represented by the formula —$NR^{4b}$— wherein $R^{4b}$ represents a hydrogen atom or a $C_1$-$C_6$ alkyl group.

5. A compound represented by the following formula, a salt thereof or a hydrate of them:

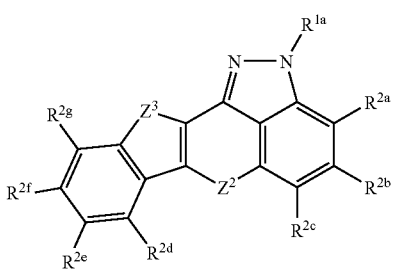

(V)

wherein $R^{1a}$, $R^{2a}$, $R^{2b}$ and $R^{2c}$ have the same meanings as $R^{1a}$, $R^{2a}$, $R^{2b}$ and $R^{2c}$ described in claim 1, respectively; $Z^2$ represents a 1,2-ethylene group which may be substituted, a 1,2-vinylene group which may be substituted, an oxymethylene group which may be substituted, an aminomethylene group which may be substituted, an amide group which may be substituted, or an ester group; $R^{2d}$, $R^{2e}$, $R^{2f}$ and $R^{2g}$ each independently represent a substituent selected from the Substituent Group (a) described in claim 1; and $Z^3$ represents a nitrogen atom, an oxygen atom, a sulfur atom or a group represented by the formula —$NR^{4b}$— wherein $R^{4b}$ repesents a hydrogen atom or a $C_1$-$C_6$group.

6. A compound represented by the following formula, a salt thereof or a hydrate of them:

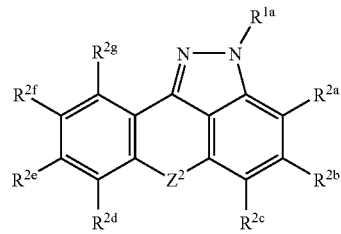

(VI)

wherein $R^{1a}$, $R^{2a}$, $R^{2b}$ and $R^{2c}$ have the same meanings as $R^{1a}$, $R^{2a}$, $R^{2b}$ and $R^{2c}$ described in claim 1, respectively; $Z^2$ represents a 1,2-ethylene group which may be substituted, a 1,2-vinylene group which may be substituted, an oxymethylene group which may be substituted, an aminomethylene group which may be substituted, an amide group which may be substituted, or an ester group; and $R^{2d}$, $R^{2e}$, $R^{2f}$ and $R^{2g}$ each independently represent a substituent selected from the Substituent Group (a) described in claim 1, provided that 6,7-dihydrobenzo[1,2]cyclohepta[3,4,5-cd]indazole is excluded.

7. The compound according to any one of claims 3 to 6, a salt thereof or a hydrate of them, wherein at least five of $R^{2a}$, $R^{2b}$, $R^{2c}$, $R^{2d}$, $R^{2e}$, $R^{2f}$ and $R^{2g}$ are hydrogen atoms.

8. The compound according to claim 2, a salt thereof or a hydrate of them, wherein $Z^2$ is a 1,2-ethylene group, a 1,2-vinylene group, a group represented by the formula —CO—$NR^{4a}$— wherein $R^{4a}$ represents a hydrogen atom or a $C_1$-$C_6$ alkyl group or a group represented by the formula —$NR^{4a}$—CO— wherein $R^{4a}$ represents a hydrogen atom or a $C_1$-$C_6$ alkyl group.

9. The compound according to claim 1 or 2, a salt thereof or a hydrate of them, wherein the ring A is a benzene ring which may have one to three groups selected from the Substituent Group (a) described in claim 1, a naphthalene ring which may have one to three groups selected from the Substituent Group (a) described in claim 1, an indole ring which may have one to three groups selected from the Substituent Group (a) described in claim 1, a benzofuran ring which may have one to three groups selected from the Substituent Group (a) described in claim 1, a benzothiophene ring which may have one to three groups selected from the Substituent Group (a) described in claim 1, a pyridine ring which may have one to three groups selected from the Substituent Group (a) described in claim 1, a furan ring which may have one to three groups selected from the Substituent Group (a) described in claim 1, or a thiophene ring which may have one to three groups selected from the Substituent Group (a) described in claim 1.

10. The compound according to claim 1 or 2, a salt thereof or a hydrate of them, wherein the ring A is a ring having one group selected from the Substituent Group (a) described in claim 1.

11. The compound according to claim 1, a salt thereof or a hydrate of them, wherein $R^{1a}$ is a hydrogen atom.

12. The compound according to claim 1, a salt thereof or a hydrate of them, wherein $R^{2a}$ and $R^{2b}$ are hydrogen atoms.

13. A c-Jun amino-terminal kinase (JNK) inhibitor, comprising the compound according to claim 1, a salt thereof or a hydrate of them.

14. A c-Jun amino-terminal kinase 1 (JNK 1), c-Jun amino-terminal kinase 2 (JNK 2) and/or c-Jun amino-terminal kinase 3 (JNK 3) inhibitor, comprising the compound according to claim 1, a salt thereof or a hydrate of them.

* * * * *

UNITED STATES PATENT AND TRADEMARK OFFICE
CERTIFICATE OF CORRECTION

PATENT NO. : 7,390,797 B2
APPLICATION NO. : 10/503216
DATED : June 24, 2008
INVENTOR(S) : Norihito Ohi et al.

It is certified that error appears in the above-identified patent and that said Letters Patent is hereby corrected as shown below:

On the Title Page, correct item (73) to read as follows:

(73) Assignee: EISAI R&D MANAGEMENT CO., LTD., Bunkyo-ku, Tokyo (JP)

Signed and Sealed this

Twenty-fourth Day of March, 2009

JOHN DOLL
*Acting Director of the United States Patent and Trademark Office*